United States Patent
Fagerberg et al.

(10) Patent No.: US 9,655,839 B2
(45) Date of Patent: May 23, 2017

(54) PROBIOTIC ARGINOLYTIC ORAL COMPOSITIONS AND METHODS OF MAKING AND USING PROBIOTIC ARGINOLYTIC ORAL COMPOSITIONS

(71) Applicant: University of Florida Research Foundation, Inc., Gainesville, FL (US)

(72) Inventors: Marcelle Matos Nascimento Fagerberg, Gainesville, FL (US); Robert A. Burne, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/767,181

(22) PCT Filed: Feb. 12, 2014

(86) PCT No.: PCT/US2014/016139
§ 371 (c)(1),
(2) Date: Aug. 11, 2015

(87) PCT Pub. No.: WO2014/127066
PCT Pub. Date: Aug. 21, 2014

(65) Prior Publication Data
US 2015/0366792 A1    Dec. 24, 2015

Related U.S. Application Data

(60) Provisional application No. 61/764,579, filed on Feb. 14, 2013.

(51) Int. Cl.
| | | |
|---|---|---|
| *A61K 8/99* | (2006.01) | |
| *A61K 31/198* | (2006.01) | |
| *A61K 31/7004* | (2006.01) | |
| *A61K 35/741* | (2015.01) | |
| *A61Q 11/00* | (2006.01) | |
| *C12Q 1/14* | (2006.01) | |

(52) U.S. Cl.
CPC ............. *A61K 8/99* (2013.01); *A61K 31/198* (2013.01); *A61K 31/7004* (2013.01); *A61K 35/741* (2013.01); *A61Q 11/00* (2013.01); *C12Q 1/14* (2013.01); *G01N 2333/315* (2013.01)

(58) Field of Classification Search
None
See application file for complete search history.

(56) References Cited

U.S. PATENT DOCUMENTS

| | | |
|---|---|---|
| 2002/0094328 A1 | 7/2002 | De Simone |
| 2007/0212311 A1 | 9/2007 | Burne et al. |
| 2011/0085990 A1 | 4/2011 | Sullivan et al. |

FOREIGN PATENT DOCUMENTS

WO    WO2012028759    3/2012

OTHER PUBLICATIONS

Dong et al. Applied and Environmental Microbiology, 68:5549-553, 2002.*
Dong et al. Journal of Bacteriology, Apr. 2004, p. 2511-2514, 186 (8): 2511-2514.*
Liu et al. Characterization of Arginolytic Microflora of Human Oral Biofilms. AADR Annual Meeting, Poster Session Abstract, Saturday Mar. 24, 2012.*
Kreth et al. Journal of Bacteriology, Jul. 2008, p. 4623-4640 vol. 190, No. 13.*
Christopher et al. Microbiology (2010), 156, 3469-3477.*
Nascimento et al. Oral Microbiol Immunol. Author Manuscript, available in PMC 2010 Apr. 1 pp. 1-16.*
Burne et al. FEMS Microbiology Letters 193 (2000) 1-6.*
International Search Report for PCT/US2014/016139 mailed May 28, 2014.
Liu, Y. et al., 'Multiple two-component systems modulate alkali generation in Streptococcus gordonii in response to environmental stresses', Journal of Bacteriology, 2009, vol. 191, No. 23, pp. 7353-7362.
Clancy, K. A. et al., 'Characterization of recombinant, ureolytic Streptococcus mutans demonstrates an inverse relationship between dental plaque ureolytic capacity and cariogenicity', Infect ion and Immunity, 2000, vol. 68, No. 5, pp. 2621-2629.
International Search Report dated Jul. 22, 2016, Application No. EP14750993; European Patent Office, Munich, Germany; 10 pages.
Nascimento, MM, et al. "Correlations of oral bacterial arginine and urea catabolism with caries experience". Oral Microbiology and Immunology; 2009: 24: pp. 89-95; John Wiley & Sons NS.
Liu, Ya-Ling, et al; "Progress toward understanding the contribution of alkali generation in dental biofilms to inhibition of dental caries"; International Journal of Oral Science (2012) 4, pp. 135-140; www.nature.com/ijos.
Gordan, V.V. et al; "Could Alkali Production Be Considered an Approach for Caries Control?" Caries Research; 2010; 44: pp. 547-554; 8 pages.
Ialasvuori, Heli, et al.; "Probiotic Lactobacillus reuteri strains ATCC PTA 5289 and ATCC 55730 differ in their cariogenic properties in vitro"; Department of Cariology, Institute of Dentistry, University of Turku, Turlw, Finland; Archives of Oral Biology 57 (2012) pp. 1633-1638.

\* cited by examiner

*Primary Examiner* — Oluwatosin Ogunbiyi
(74) *Attorney, Agent, or Firm* — Thomas Horstemeyer, LLP

(57) ABSTRACT

The present disclosure provides probiotic arginolytic oral compositions, methods of making probiotic arginolytic oral compositions, and methods of using probiotic arginolytic oral compositions to increase arginolytic activity in the oral cavity and/or to treat and/or prevent caries.

5 Claims, 11 Drawing Sheets

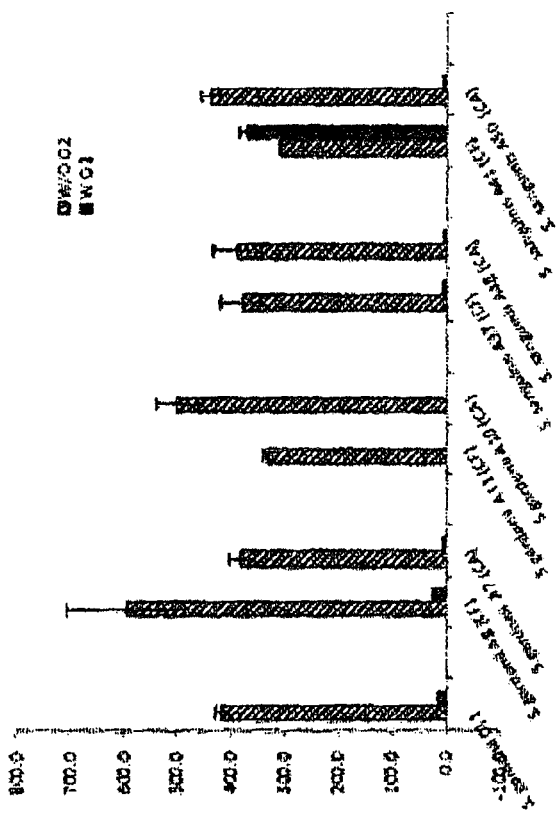
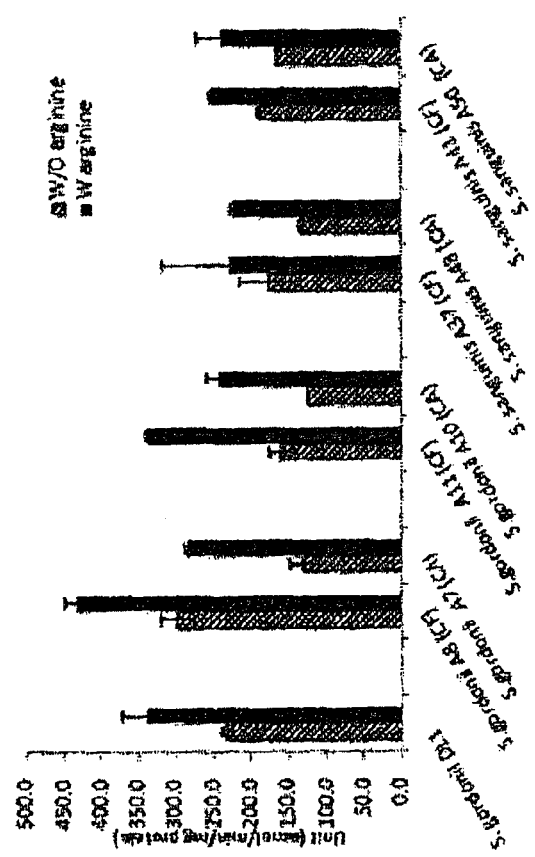
Figure 3D
Figure 3C

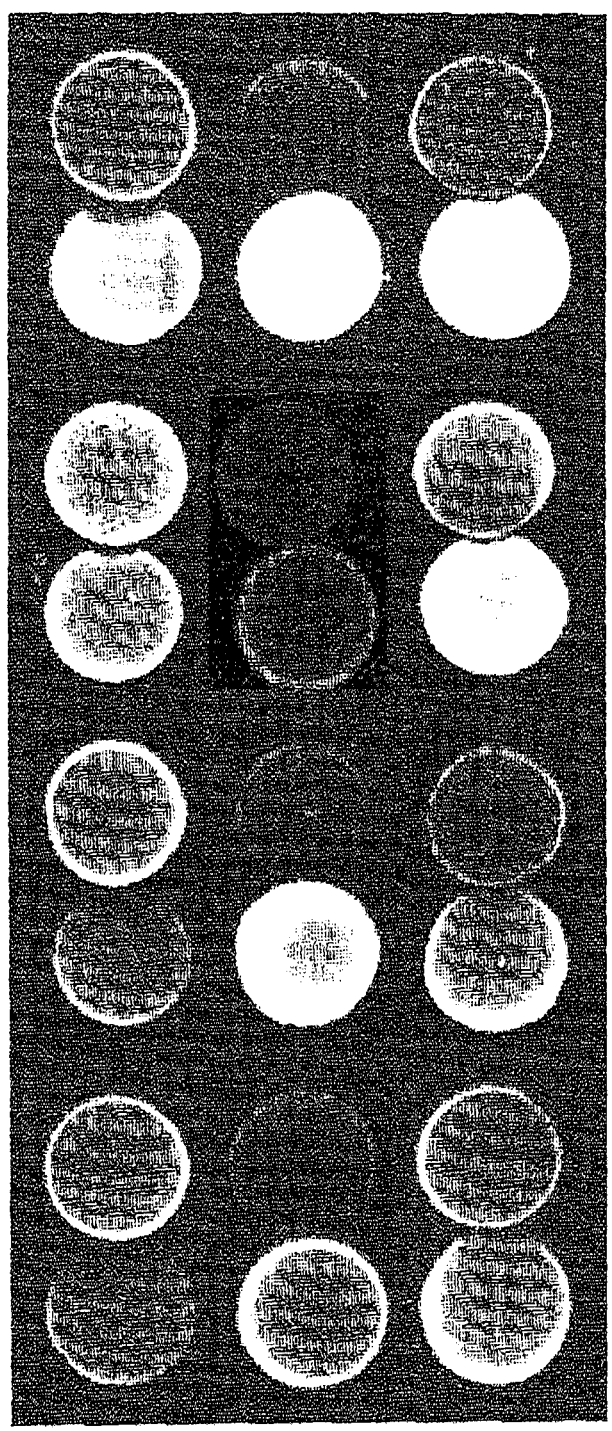

*S. gordonii* str. Challis Substr.CH1 A9 (CF)

S. sanguinis JCM 5708 A33 (CF)

PROBIOTIC ARGINOLYTIC ORAL COMPOSITIONS AND METHODS OF MAKING AND USING PROBIOTIC ARGINOLYTIC ORAL COMPOSITIONS

CROSS-REFERENCE TO RELATED APPLICATIONS

This application is the 35 U.S.C. §371 national stage application of PCT Application No. PCT/US2014/016139, filed Feb. 12, 2014, which claims priority to U.S. provisional application entitled, "Probiotic Oral Compositions and Methods of Using Probiotic Oral Compositions," having Ser. No. 61/764,579, filed on Feb. 14, 2013, both of which are entirely incorporated herein by reference.

STATEMENT REGARDING FEDERALLY SPONSORED RESEARCH OR DEVELOPMENT

This invention was made with Government support under Contract No.: DE10362 awarded by the National Institute of Dental and Craniofacial Research. The Government has certain rights in this invention.

SEQUENCE LISTING

The instant application contains a sequence listing which has been submitted with the instant application via EFS-Web. The sequence listing file is named 01974537.txt, is 794 bytes in size, and is incorporated herein by reference in its entirety.

BACKGROUND

Dental caries is the most prevalent infectious and chronic disease affecting humans, and is associated with costly treatment worldwide. The transition from dental health to dental caries is characterized by compositional and metabolic changes in the complex microbial communities of oral biofilms. Oral biofilms, often called dental plaque, constantly form and grow on all tooth surfaces. Although production of acid by the bacteria in oral biofilms is the direct cause of dental caries, it is noteworthy that increases in the proportions of aciduric organisms appear to occur at the expense of species that are less acid tolerant (i.e. less "aciduric"). Of particular note, a subset of less aciduric organisms derives protection from plaque acidification by alkali generation, which shows a positive association with dental health.

One of the primary routes for alkali generation by oral bacteria is the arginine deiminase system (ADS), through which arginine is catabolized into ornithine, ammonia and $CO_2$, with the concomitant generation of ATP. Hence, the ADS serves key physiological functions in bacteria, providing protection from the deleterious effects of low pH and ATP for growth and maintenance. The ADS activity in oral biofilms can impact the ecology of oral microbial communities by moderating the pH through ammonia production.

A variety of bacteria that colonize the teeth and oral soft tissues and form oral biolfims express the ADS. An increased risk for dental caries has been associated with a reduced ability of oral biofilms to produce alkali from arginine via the arginine deiminase system (ADS). Specifically, plaque bacteria from caries-free subjects present higher levels of ADS activity when compared to plaque bacteria from caries-active subjects. Moreover, there is a high degree of variability in the rate of alkali production among individuals, in some cases greater than 1000-fold. A better understanding of the microbiological basis of inter-subject variation in ADS activity and methods for improving ADS activity for the improvement of oral health would be beneficial.

SUMMARY

Briefly described, embodiments of the present disclosure provide probiotic arginolytic oral compositions, methods of making probiotic arginolytic oral compositions, and methods of using probiotic arginolytic oral compositions to increase arginolytic activity in the oral cavity and/or to treat and/or prevent caries.

Embodiments of an arginolytic probiotic oral composition of the present disclosure include a mixture of isolated bacterial strains and a pharmaceutically acceptable oral carrier. In embodiments, the mixture includes at least two different isolated arginolytic bacterial strains, each strain capable of producing ammonia via the arginine deiminase system (ADS) and each strain meeting at least one of the following criteria: expressing ADS activity in the absence of environmental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries, where at least two of the criteria are met by the mixture of bacterial strains.

Embodiments of methods of making a mixture of arginolytic bacterial strains for oral use include at least the following steps: (a) obtaining a mixture of bacterial strains isolated from oral samples; (b) isolating and identifying arginolytic bacterial strains capable of producing ammonia via the arginine deiminase system (ADS); (c) conducting one or more separate assays to identify arginolytic bacterial strains capable of expressing ADS activity in at least one of the following assay conditions: in the absence of environmental arginine, in the presence of glucose, in a non-acidic pH, in aerobic conditions, and in the presence of at least one bacterial strain associated with dental caries; (d) selecting at least two different isolated arginolytic bacterial strains identified in step (c) to prepare a mixture of arginolytic bacteria, where the mixture expresses ADS activity in at least two of the conditions.

In embodiments, the present disclosure provides methods of preventing or reducing the incidence of dental caries to a host and methods of slowing or arresting the progression of dental caries lesions in a host. The methods include administering to a host a probiotic oral composition including a mixture of isolated bacterial strains and a pharmaceutically acceptable oral carrier, where the mixture includes at least two different isolated arginolytic bacterial strains, each strain capable of producing ammonia via the arginine deiminase system (ADS) and each strain meeting at least one of the following criteria: expressing ADS activity in the absence of environmental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries, where at least two of the criteria are met by the mixture of bacterial strains.

The present disclosure also provides embodiments of methods of increasing the amount of ammonia-producing bacteria in the oral cavity of a host, the methods including administering to a host a probiotic oral composition including a mixture of isolated bacterial strains and a pharmaceutically acceptable oral carrier, where the mixture includes at least two different isolated arginolytic bacterial strains, each strain capable of producing ammonia via the arginine deiminase system (ADS) and each strain meeting at least one of the following criteria: expressing ADS activity in the absence of environmental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries, where at least two of the criteria are met by the mixture of bacterial strains.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A-3D are a series of bar graphs illustrating comparisons of the ADS activity levels of arginolytic isolates from caries-active and caries-free subjects grown under different environmental conditions: different sugars (FIG. 3A), different pH (FIG. 3B), the presence or absence of arginine (FIG. 2C), and aerobic vs. anaerobic conditions (FIG. 3D). Results represent the mean and standard deviations (error bars) of three independent experiments.

FIGS. 4A-4D are a series of digital images illustrating an assay showing inhibitory effects of *S. gordonii* DL1 (FIG. 4A) and ADS-positive isolates *S. gordonii* A8 (FIG. 4B), *S. australis* A12 (FIG. 4C), and *S. sanguinis* A33 (FIG. 4D) on the growth *S. mutans* UA159.

DESCRIPTION

Figure 1:
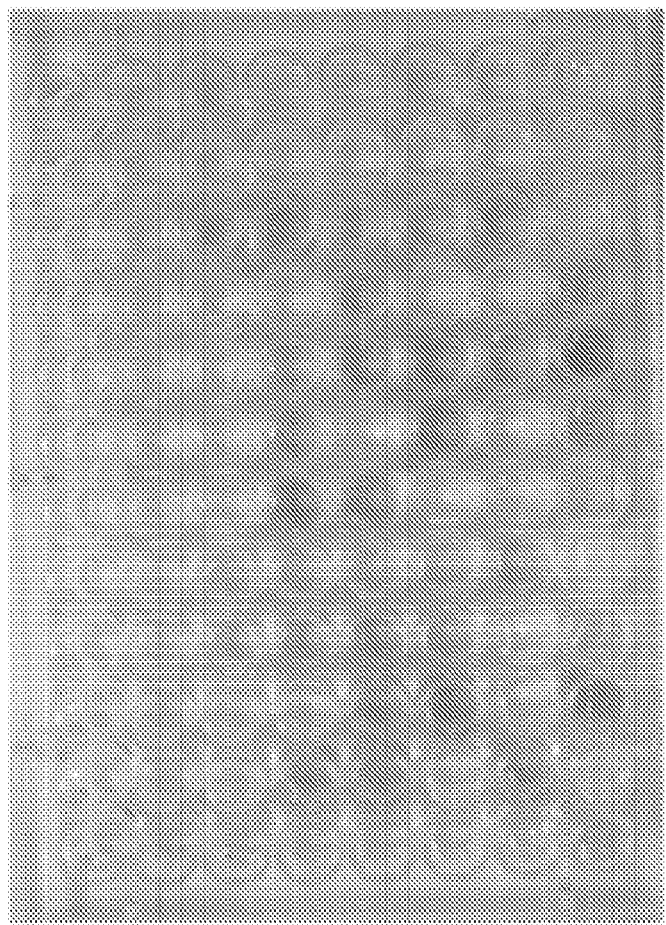
FIG. 1 illustrates a digital image of a screening of ADS-positive bacterial strains from dental plaque. ADS-positive phenotype is revealed by yellow-orange color when the Nessler's reagent detects the ammonia generated.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, dentistry, biology, microbiology, statistics, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

DEFINITIONS

In describing the disclosed subject matter, the following terminology will be used in accordance with the definitions set forth below.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

As used herein the term "microbiome" refers to the living environment of microorganisms within a host organism. As used herein, "microbiome" generally refers to the community of microorganisms (e.g., bacteria) living within a host organism, such as within the oral cavity of a host organism. The term "microflora" similarly refers to the collective organisms living within the microbiome, the terms may be used interchangeably in the present disclosure. The term native microbiome also refers to the bacterial community of a host that has not been altered by (or prior to alteration by) the administration of drugs (e.g., antibiotics or probiotics) or procedures intended to alter the composition of the native bacterial colony. The native bacterial community of a host can change over time due to various natural and synthetic causes (e.g., illness, changes in diet, drugs, medical procedures, and the like).

The terms "taxonomic category" or "taxonomic classification" or "classification" as used herein refers to the categorization of organisms into the scientifically established taxonomic categories into which they have been assigned (e.g., kingdom, phylum, class, order, family, genus, species, strain), or, in the case of previously unidentified organisms, the category to which they would likely be assigned according to established scientific procedures based on similarity of genetics or characteristics. The "taxonomic category" may be a broad category (e.g., phylum, class) or a narrower category (e.g., genus, species), and the act of classification may involve multiple organisms or only one. "Classification" may also involve the act of grouping individuals into categories based on like characteristics, but generally, in the present disclosure "classification" refers to taxonomic classification" unless the context indicates otherwise.

A "strain" as used herein refers to a taxonomic subgrouping within the species level, where a strain is a genetic variant or sub-type within a species. In the present disclosure a "strain" may refer to a clinical isolate that has close sequence identity (e.g., about 95% sequence identify, about 99% sequence identity, etc.) to a known species, but that may differ in one or more characteristics, such as, but not limited to, ADS activity level in certain environmental conditions.

An "isolated bacterial strain" or "bacterial isolate" refers to a bacterial strain or culture that has been produced from a bacterial organism that was isolated from a natural, heterogeneous environment (e.g., a host oral cavity) or population of microorganisms and separated via known microbiological techniques from the community of other microorganisms in its environment of origin. The isolated strain may then be grown in culture. An isolated bacterial strain or culture of the isolated bacterial strain is not necessarily free of all possible impurities, but it is a substantially homogenous culture of the bacterial isolate and can be distinguished from a naturally occurring, heterogeneous group of microorganisms.

As used herein, a "probiotic bacterium" refers to a bacterium that is generally regarded by the medical community as non-pathogenic and that confers a health benefit to the host. For instance, a bacterium that appears to have high ADS activity and thus promote an oral environment with reduced incidence of caries and that is not toxic to the host would be a non-limiting example of probiotic bacterium in the present disclosure.

As used herein "ADS activity" refers to the ability of a bacterial strain to produce alkali in the form of ammonia via the arginine deiminase system (ADS). The "ADS activity level" refers to the amount of ammonia a bacterial strain can produce via the ADS system. In embodiments, the ADS activity level is determined as nmol of citrulline generated (minute×mg protein)$^{-1}$. "Expressing ADS activity" or "expressing sufficient ADS activity" refers to the ability of some bacterial strains to metabolize arginine via the ADS at standard growth conditions or at growth under one or more adverse environmental factors, such as, but not limited to, non-acidic pH, low environmental arginine, high carbohydrate conditions (e.g., in presence of glucose), or aerobic conditions (e.g., the presence of oxygen). In embodiments, the ability of a strain to express ADS activity is determined with respect to the ADS activity of a known, well-characterized ADS-positive strain (e.g., *S. gordonii* DL1) under the same environmental assay conditions (e.g., under "standard growth conditions" or some other variation of growth conditions). In embodiments, if the strain expresses about the same activity, a greater activity, or a set percentage of ADS activity with respect to *S. gordonii* DL1, under the same assay conditions, the strain "expresses sufficient ADS activity". In other embodiments, the ability of a strain to express ADS activity under certain environmental conditions can be determined with respect to the ADS activity of the same strain. In some such embodiments, a strain is said to "express ADS activity" under the environmental assay conditions if it has a certain percentage of ADS activity (e.g., at least about 25% ADS activity, at least about 40% ADS activity, at least about 50% ADS activity, at least about 75% ADS activity, etc.) as compared to the ADS activity of that strain under standard growth conditions. In the present disclosure, "standard growth conditions", is a TY medium (tryptone-yeast extract broth) containing 25 mM galactose and 10 mM supplemental arginine at 5% $CO_2$, at 37° C. to an optical density at OD600+0.5-06.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying, slowing, or arresting disease progression, substantially preventing spread of disease, reducing, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease. With respect to caries, "treating" includes reducing the appearance of dental caries lesions and slowing or arresting the progression of dental caries lesions (e.g., slowing or stopping the growth or severity of the lesions). "Treating" also includes "preventing"/"prophylactically treating." As used herein, the terms "prevent", "prophylactically treat," or "prophylactically treating" refers to completely, substantially, or partially preventing a disease/condition or one or more symptoms thereof in a host. Similarly, "delaying the onset of a condition" can also be included in "prophylactically treating", and refers to the act of increasing the time before the actual onset of a condition in a patient that is predisposed to the condition. With respect to caries, "preventing" or "prophylactic treatment" can include preventing the appearance of new caries lesions in a host.

By "administration" is meant introducing a compound of the present disclosure into a subject; it may also refer to the act of providing a composition of the present disclosure to a subject (e.g., by prescribing). The preferred route of administration of the compositions of the present disclosure is oral. However, any route of administration that will assist the composition to treat the oral condition of the host can be used.

The term "organism," "subject," or "host" refers to any living entity in need of treatment, including humans, mammals (e.g., cats, dogs, horses, chicken, pigs, hogs, cows, and other cattle), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host. Hosts that are "predisposed to" condition(s) can be defined as hosts that do not exhibit overt symptoms of one or more of these conditions but that are genetically, physiologically, or otherwise at risk of developing one or more of these conditions.

As used herein, the following terms have the meanings ascribed to them unless specified otherwise. In this disclosure, "consisting essentially of" or "consists essentially" or the like, when applied to methods and compositions encompassed by the present disclosure, refers to compositions like those disclosed herein but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments. Specifically, with respect to mixtures of arginolytic bacterial strains of the present disclosure, "consisting essentially of" indicates that minor amounts of other bacterial strains other than those with the criteria listed may be present in minor amounts, but that they do not affect the overall function of the mixture and do not affect the arginolytic activity of the mixture.

Discussion

The embodiments of the present disclosure encompass probiotic, arginolytic oral compositions, methods of making a mixture of arginolytic bacterial strains for oral use, methods and compositions for treating and/or preventing dental caries and slowing and/or arresting the progression of caries lesions in a patient, and methods and compositions for increasing the amount of arginolytic bacteria in the oral cavity of a host and increasing ammonia production in the oral cavity of a host. Embodiments of the present disclosure include compositions including a mixture of arginolytic bacterial strains. In embodiments, the compositions are probiotic oral compositions.

Evidence continues to accumulate from in vitro and clinical observations that support the role of alkali generation in oral ecology and inhibition of dental caries (Dawes and Dibdin, 2001; Margolis et al., 1988b; Nascimento et al., 2009a; Peterson et al., 1985; Shu et al., 2007a; Wijeyeweera and Kleinberg, 1989a). A positive correlation between oral arginine metabolism and absence of caries activity has been clinically demonstrated in adults (Nascimento et al., 2009a), and more recently in children (Nascimento et al., 2012). Specifically, oral bacteria from dental plaque of caries-free subjects presents higher ADS activity compared with those from caries-active subjects. There is also a high degree of variability in the rate of ammonia production among individuals, in some cases greater than 1000-fold. Previous studies using laboratory strains of oral streptococci indicate that the expression of ADS genes is substrate inducible, sensitive to carbon catabolite repression (CCR), and thrives low pH and anaerobic conditions. Specific and global transcriptional regulators, multiple two-component systems (TCS) and other factors have been shown to regulate ADS activity through transcriptional and post-transcriptional mechanisms (Burne, 1991; Dong et al., 2004; Liu and Burne, 2009; Liu et al., 2008). An in vitro study showed that as little as a five-fold decrease in the ammonia-generating capacity of a genetically-modified strain of the caries pathogen *Streptococcus mutans* resulted in the loss of ability to offset environmental acidification by glycolysis (Clancy et al., 2000). Therefore, many individuals may lack sufficient ADS activity to neutralize dental plaque during fasting periods or following a cariogenic challenge. Thus, the ADS activity of plaque bacteria can impact the pH profiles of resting and carbohydrate-challenged plaque, and therefore, the risk for caries development.

Differences in the microbial composition of oral biofilms and differential expression of the ADS are the most likely factors that affect the capacity of oral samples from different individuals to metabolize arginine. The use of qPCR in a previous clinical study (Nascimento et al., 2009a) did not reveal a statistically significant association between the proportions of two recognized arginolytic species, *S. sanguinis* and *S. gordonii* and the caries-status of adults. These results suggested that the diminution in ADS activity associated with caries experience may not be due simply to lower proportions of known ADS-positive bacteria, and also raised the possibility that species other than those examined may contribute to overall oral ADS activity. It is also possible that environmental conditions and host factors encourage differential expression of the ADS in caries-active versus caries-free subjects. Thus, in the present disclosure, the organisms that contribute to arginolysis in the oral cavity were more thoroughly characterized and studied. Providing new insight into the fundamental microbiology and ecology of oral arginolytic bacterial communities and their relationship to dental health and dental caries, the examples below demonstrate isolation and characterization of arginolytic bacterial strains from supragingival dental plaque of caries-free and caries-active adult subjects, and the responses of these isolates to environmental stimuli.

As discussed briefly above and in greater detail below, some bacteria have the ability to produce ammonia via the arginine deiminase system (ADS). Such "arginolytic" bacteria, when found in a host (particularly the oral cavity of a host) can be beneficial in increasing ammonia production in the oral cavity of a host, thereby providing an environmental factor for reducing the incidence of caries. Some such bacterial strains are found more prevalently in the oral biofilms of caries-free individuals. As described below, the studies in the examples identified various bacterial strains capable of ADS activity and described methods for identification of various strains capable of ADS activity. Additionally, the studies described in the examples below further identified and described how to identify bacterial strains capable of maintaining ADS activity in the presence of conditions traditionally associated with a reduction in ADS activity. Many such conditions are also associated with higher incidence of caries. Thus, the ability to identify strains meeting certain criteria and expressing ADS activity in the presence of certain conditions is beneficial for increasing the level of these bacteria in a host and for methods of treating, preventing, slowing, or arresting the incidence of caries in a patient. In embodiments, some strains identified as having ADS activity and expressing ADS activity under certain conditions can be included in a probiotic oral composition. Such compositions can be used in embodiments of methods of the present disclosure to increase the amount of ammonia-producing bacteria in the oral cavity of a host, methods to treat or prevent caries, and/or methods to slow or arrest the progression of caries lesions in a patient with dental caries.

Probiotic Oral Compositions:

The present disclosure thus provides probiotic oral compositions including a mixture of bacterial strains, where the mixture includes at least two different isolated arginolytic bacterial strains. Each of the at least two isolated arginolytic bacterial strains in the mixture is capable of producing ammonia via the arginine deiminase system (ADS), and each strain meets at least one ADS-related criteria. In embodiments the ADS-related criteria include, but are not limited to, the following: expressing ADS activity in the absence of supplemental arginine (where "supplemental arginine" is arginine (in addition to arginine naturally present in the growth medium), (e.g., greater than about 5 mM of arginine) added to the base growth medium), expressing ADS activity in the presence of glucose (e.g., addition of glucose to base growth medium), expressing ADS activity in a non-acidic pH (e.g., pH of at least about 7), expressing ADS activity under aerobic conditions (e.g., in the presence of additional oxygen), inhibiting the growth of at least one bacterial strain associated with dental caries, and resisting inhibition of growth by at least one bacterial strain associated with dental caries. In embodiments of the probiotic oral compositions of the present disclosure, at least two of the above criteria are met by the mixture of bacterial strains, and each bacterial strain in the mixture may meet more than one of the criteria.

As most bacterial species associated with dental carries are not arginolytic, there will likely not be much overlap between such species. However, for clarification, in embodiments, the mixture of isolated arginolytic bacterial strains specifically excludes any strains of bacteria from a bacterial species associated with dental caries (e.g., *S. mutans* and the like). In embodiments of the compositions of the oral compositions of the present disclosure, the mixture consists of at least two different isolated arginolytic bacterial strains, with each strain capable of producing ammonia via the ADS and each strain meeting at least one of the criteria listed above.

The probiotic compositions of the present disclosure also can include a pharmaceutically acceptable oral carrier, such as, but not limited to, water, other pharmaceutically acceptable liquids, gels, powders, and the like. The compositions can be formulated into oral formulations such as, but not limited to, liquid mouth rinses, oral sprays, gels, pastes (e.g., toothpaste), certain foodstuffs, candies/mints, gum, or chewable tablets, and the like. Methods of producing such formulations are known to those of skill in the art of pharmacology and/or compounding.

In embodiments the bacterial strains for the mixture can be selected from any ADS positive bacterial strain identified or capable of identification by the methods of the present disclosure described below that show ADS activity. In embodiments arginolytic bacterial strains can be selected from strains, such as, but not limited to those identified in Tables 1 and 2 below that show ADS activity. In embodiments, the ADS activity is at least about 225 units (mg protein)$^{-1}$, at least about 250 units (mg protein)$^{-1}$, at least about 275 units (mg protein)$^{-1}$, at least about 300 units (mg protein)$^{-1}$, and so on, as measured by ADS assays under standard growth conditions, such as the ADS assay described below in Example 1. Briefly, an embodiment of an ADS assay includes measuring activity by monitoring citrulline production from arginine, as described in Example 1, below. Cells are harvested by centrifugation, washed with 10 mM Tris-maleate buffer (pH 6.8) and resuspended using ¹/₁₀ the original culture volume in the same buffer. The cells were permeablized by vortexing them with toluene and were collected by centrifugation at 18,000×g. The supernatant fluid was discarded and the pellet resuspended in 10 mM Tris-maleate buffer and used to measure AD activity in a reaction mixture containing 20 nM arginine, 10 mM hexanoic acid, and 50 mM Tris-maleate buffer (pH 6.0). The concentration of protein used in each assay was determined as described in Example 1.

In some embodiments, the ADS activity is at least about the same as the ADS activity of the well-characterized lab strain *Streptococcus. gordonni* DL1 (*Streptococcus gordonii* (strain Challis/ATCC 35105/CH1DL1/V288)) under standard growth conditions. In some embodiments the ADS activity is at least about 300 nmol of citrulline (minute×(mg of protein))$^{-1}$ (see table 1: ADS activity of *S. gordonii* DL1 of about 339.3+/−33.0) under standard growth conditions. In some embodiments, the bacterial strains for the mixture have an ADS activity of about 50% to about 100% of the activity of *S. gordonii* DL1 under standard growth conditions. In some embodiments the ADS activity of the bacterial strain is less than that of *S. gordonii* under standard growth conditions but is greater than the ADS activity of *S. gordonii* under other environmental conditions, as described in more detail below.

In some embodiments of the probiotic oral composition of the present disclosure, the bacterial strains are selected from arginolytic strains of bacteria from the species including, but not limited to, *Streptococcus parasanguinis, Streptococcus intermedius, Streptococcus gordonii, Streptococcus australis, Streptococcus sanguinis*, and *Streptococcus cristatus*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. AB690250.1), *S. gordonii* str. Challis sbustr. CH1 (Accession No. NR_074516.1), *S. gordonii* ATCC 10558 (Accession No. AY485606.1), *Streptococcus australis* Al-1 (Accession No. JX861483.1), *Streptococcus sanguinis* JCM 5708 (Accession NO. AB596946.1), and *Streptococcus cristatus* F0329 (Accession No. AY005047.1). In some embodiments the probiotic oral compositions include bacterial strains selected from the following strains identified in Table 1 (Example 1), below: *Streptococcus parasanguinis* A1, *Streptococcus intermedius* A2, *S. intermedius* A3, *S. intermedius* A5, *Streptococcus gordonii* A7, *S. gordonii* A8, *S. gordonii* A9, *S. gordonii* A 10, *S. gordonii* A11, *Streptococcus australis* A12, *S. australis* A13, *Streptococcus sanguinis* A41, and *Streptococcus cristatus* A55.

In embodiments, at least one strain in the mixture expresses ADS activity in the presence of glucose (e.g., glucose (e.g., about 25 mM glucose) instead of galactose in the growth medium). In embodiments, bacterial strains that express ADS activity in the presence of glucose that are selected for the mixture have at least about the level of ADS activity as *S. gordonii* DL1, or greater, under the same glucose conditions, or, at least about 50%, at least about 75%, at least about 90%, at least about 100% of the ADS activity of *S. gordonii* under the same glucose conditions. In some embodiments, at least one strain in the mixture that expresses ADS activity under added glucose conditions (e.g., 25 mM glucose instead of galactose added to growth medium) has at least about 25% of the ADS activity of the same strain under standard growth conditions. In embodiments, the strain that expresses ADS activity under added glucose conditions has at least about 40%, at least about 50%, at least about 75%, and so on, of the ADS activity of the same strain under standard growth conditions. In embodiments, the strains expressing ADS activity in the presence of glucose are selected from strains from bacterial species including, but not limited to: *Streptococcus parasanguinis, Streptococcus intermedius, Streptococcus gordonii*, and *Streptococcus australis*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. AB690250.1), *S. gordonii* str. Challis sbustr. CH1 (Accession No. NR_074516.1), *S. gordonii* ATCC 10558 (Accession No. AY485606.1), and *Streptococcus australis* Al-1 (Accession No. JX861483.1). Some representative bacterial strains express ADS activity of greater than DL1 (e.g., ADS>about 52.5 units) in the presence of glucose include but are not limited to the following strains: *S. parasanguinis* A1, *S. intermedius* A2, *S. intermedius* A3, S. intermedius A5, S. gordonii A7, S. gordonii A8, S. gordonii A9, S. gordonii A10, S. gordonii A11, S. australis A12, and S. australis A13.

In embodiments, at least one strain in the mixture expresses ADS activity in a non-acidic pH (e.g., pH at least about 7). In embodiments, bacterial strains that express ADS activity in a non-acidic pH that are selected for the mixture have at least about the level of ADS activity as S. gordonii DL1, or greater, under the same pH conditions, or at least about 75% of the ADS activity as S. gordonii DL1 under the same pH conditions. In embodiments, the bacterial strains have at least about 50% of the ADS activity as S. gordonii DL1 under the same pH conditions. In some embodiments, at least one strain in the mixture that expresses ADS activity in a non-acidic pH has at least about 50% of the ADS activity of the same strain under standard growth conditions, or under an acidic pH of about 5.7. In embodiments, the strain that expresses ADS activity under a non-acidic glucose conditions has at least about 40%, at least about 50%, at least about 75%, and so on, of the ADS activity of the same strain under standard growth conditions, and/or with an acidic pH of about 5.7. In embodiments, the strains expressing ADS activity in non-acidic pH are selected from strains from bacterial species including, but not limited to: *Streptococcus parasanguinis, Streptococcus intermedius, Streptococcus gordonii*, and *Streptococcus australis*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. NR_074516.1), and *Streptococcus australis* Al-1 (Accession No. JX861483.1). Some representative bacterial strains that express ADS activity of greater than DL1: (ADS>about 344.5 units) in a non-acidic pH include, but are not limited to the following strains: S. parasanguinis A1, S. intermedius A2, S. intermedius A3, S. gordonii A8, and S. australis A12.

In embodiments, at least one strain in the mixture expresses ADS activity in the absence of supplemental arginine (e.g., less than about 5 mM arginine added to the growth medium). In embodiments, bacterial strains that express ADS activity in the absence of supplemental arginine have at least the level of ADS activity as S. gordonii DL1, or greater, under the same arginine-deficient conditions, or have at least 40%, at least 50%, at least 75%, and so on, of ADS activity as S. gordonii DL1 under the same arginine-deficient conditions. In embodiments, the strain that expresses ADS activity in the absence of supplemental arginine has at least about 60% of the ADS activity of the same strain under standard growth conditions. In embodiments, the strain that expresses ADS activity in the absence of supplemental arginine conditions has at least about 40%, at least about 50%, at least about 75%, and so on, of the ADS activity of the same strain under standard growth conditions. In embodiments, the strains expressing ADS activity in the absence of environmental arginine are selected from strains from bacterial species including, but not limited to: *Streptococcus parasanguinis, Streptococcus intermedius, Streptococcus gordonii*, and *Streptococcus australis*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. NR_074516.1), and *Streptococcus australis* Al-1 (Accession No. JX861483.1).

Some representative strains that express ADS activity greater than DL1 (ADS>about 232.5 units) in the absence of environmental arginine include, but are not necessarily limited to the following: S. parasanguinis A1, S. intermedius A2, S. intermedius A3, S. gordonii A8, S. australis A12, and S. australis A13.

In embodiments, at least one strain in the mixture expresses ADS activity in aerobic conditions (e.g., in the presence of $O_2$, e.g., aeration induced by agitation, such as by a rotary shaker.). In embodiments, bacterial strains that express ADS activity in aerobic conditions have at least the level of ADS activity as S. gordonii DL1, or greater, under the same oxygenation, or have at least 60%, 75%, 90%, and so on of the ADS activity of S. gordonii DL1 under the same oxygenation. In embodiments strains expressing ADS activity in aerobic conditions have at least about 60% of the ADS activity of the same strain under standard growth conditions without aeration (e.g., in an anaerobic chamber). In embodiments, the strain that expresses ADS activity in aerobic conditions has at least about 40%, at least about 50%, at least about 75%, at least about 100% and so on, of the ADS activity of the same strain under standard growth conditions without aeration. In embodiments, the strains expressing ADS activity in aerobic conditions are selected from strains from bacterial species including, but not limited to: *Streptococcus parasanguinis, Streptococcus intermedius, Streptococcus gordonii, Streptococcus australis, Streptococcus sanguinis*, and *Streptococcus cristatus*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *S. gordonii* str. Challis sbustr. CH1 (Accession No. NR_074516.1), *Streptococcus australis* Al-1 (Accession No. JX861483.1), *Streptococcus sanguinis* JCM 5708 (Accession NO. AB596946.1), and *Streptococcus cristatus* F0329 (Accession No. AY005047.1). Representative bacterial strains that express ADS activity greater than DL1 (e.g., ADS>14.4 units) under aerobic conditions include, but are not limited to the following: S. parasanguinis A1, S. intermedius A2, S. intermedius A3, S. intermedius A5, S. gordonii A8, S. australis A12, S. sanguinis A41, and S. cristatus A55.

In embodiments of the probiotic oral composition of the present disclosure where a bacterial strain inhibits the growth of at least one bacterial strain associated with dental caries and/or resists inhibition of growth by at least one bacterial strain associated with dental caries, the bacterial strain associated with dental caries can be, but is not limited to, one or more strains of *Streptococcus mutans*. Other bacterial strains associated with dental caries include, but are not limited to, strains of *Streptococcus sobrinus*, various *Lactobacillus* species, certain *Scardovia* species and some *Actinomyces* species.

In embodiments of the present disclosure, the probiotic composition may also include one or more compounds to increase the ADS activity of the bacterial strains. For instance, such additional compound may be a substance that can alter an aspect of the oral environment to make the environment more conducive to ADS activity. In embodiments, the one or more compounds to increase the ADS activity of the bacterial strains can include, but are not limited to: galactose, arginine, arginine-containing peptides and proteins (e.g. those derived from foodstuffs) or an acidic compound. In embodiments of the present disclosure, the probiotic composition includes arginine. It will be understood that since these compositions are to be administered orally to a host that the components should be pharmaceutically and biologically acceptable (e.g., generally recognized as safe, non-toxic, and the like).

Other components can be included in the oral probiotic compositions of the present disclosure to improve performance or other aspects of the composition (such as taste, smell, mouth feel, and the like). It will be understood that the bacterial strains included in embodiments of the compositions of the present disclosure are isolated strains and are not merely a samples obtained from a natural environment and placed directly in an oral composition.

Methods of Selecting Arginolytic Bacterial Strains for Oral Use:

The present disclosure also provides methods of identifying and selecting arginolytic bacterial strains and making mixtures of arginolytic bacterial strains for oral use in a host. In embodiments, the methods include obtaining a plurality of bacterial strains isolated from oral samples (e.g., samples taken from a host, such as a caries free host). From the plurality of bacterial strains, assays are conducted to identify and isolate arginolytic bacterial strains capable of producing ammonia via the arginine deiminase system (ADS). Embodiments of such methods are described in the examples below. After isolating and selecting the ADS positive strains, one or more additional assays can be conducted to identify arginolytic bacterial strains capable of expressing ADS activity in environmental conditions that are generally not conducive the arginine production in a host and/or that are conducive to caries. In embodiments, assays are used to mimic such environmental conditions for identification and selection of bacterial isolates that express ADS activity under such conditions. In embodiments, the environmental assay conditions include, but are not limited to, the absence of environmental arginine, the presence of glucose, a non-acidic pH, aerobic conditions, and the presence of at least one bacterial strain associated with dental caries. In embodiments, the bacterial strain associated with dental caries is *S. mutans*. In embodiments, one or more assays for such conditions are carried out separately for strains of ADS-positive bacteria identified in the preceding step. The method further includes, selecting at least two different isolated arginolytic bacterial strains identified in the environmental condition assay step and using the selected strains to prepare a mixture of arginolytic bacterial that expresses ADS activity in at least two of the selected environmental conditions.

The ADS activity for the strains and the ability of the strain to express ADS activity under various conditions is determined as set forth above (e.g., with respect to a certain % of the ADS activity of the same strain under standard growth conditions and/or with respect to the ADS activity of the lab strain *S. gordonii* DL1 under the same environmental conditions as the selected strain).

Once the strains are selected, various mixtures of strains with ADS activity under different environmental conditions can be prepared. Such mixtures can then be used to prepare probiotic oral compositions of the present disclosure described above. The mixtures can be combined with one or more compounds capable of increasing the ADS activity of the bacterial strains (e.g., arginine, galactose, acidic compounds, and the like).

Methods of Use

The compositions described above can be used in a number of ways to affect the oral environment of a host. In embodiments, the compositions can be used to increase the amount of ammonia-producing bacteria in the oral cavity of a host, to increase the ammonia production in the oral cavity of a host, and/or to treat dental caries in patients, including both children and adults.

For instance, in embodiments, the compositions of the present disclosure can be administered to a host to increase the amount of ammonia-producing arginolytic bacteria in the oral cavity of the host. In embodiments, the composition may be administered during times when the oral environment of the host is least likely to be conducive to ADS activity in order to increase the potential for ADS activity and reduce potential for creating a caries-conducive environment. For instance, the compositions may be administered after a meal (e.g., a high-carbohydrate meal), or before sleep. In embodiments, administering the probiotic oral composition increases the amount of ammonia-producing bacteria to an amount greater than existed in the oral cavity of the host prior to administration of the composition. The increased amount of ammonia-producing bacteria may be sustained for only a short time period (e.g., a few hours), or it may persist for a longer period (e.g., several hours to days). The length of time may depend on the formulation of the composition (e.g., a mouth rinse or oral spray vs. a saliva-resistant gel or paste applied to the oral/dental surfaces or a long-lasting chewing gum or lozenge). Even if the higher level of ADS-producing bacterial persists for a relatively short time, with optimal timing, this should still be sufficient to provide benefits to a host in terms of providing a healthier oral environment to discourage caries growth.

In embodiments, the method of increasing the amount of ammonia-producing bacteria in the oral cavity of a host also increases the ammonia production in the oral cavity of the host, with respect to the amount of ammonia production prior to administration of the probiotic oral composition.

In other embodiments, the compositions can be administered to patients to help treat or prevent dental caries in a patient predisposed to dental caries, who has had a history of dental caries, or who has an active case of dental caries. In embodiments, the composition can be administered to a host with active dental caries to slow or arrest the progression of a caries lesion.

The compositions of the present disclosure can be administered to patients according to a regimen determined by their dental care provider. In embodiments of the present disclosure, the composition may be administered in a single dose or it may be administered on a regular repeating schedule. In some embodiments, the composition may be administered during regular dental visits, such as when being used for prevention. In yet other embodiments, the composition may be provided to a patient in the form of a self-administered oral formulation for administration on a regular basis for a period of time, such as daily, weekly, or some other regular schedule for a period of time such as a number of weeks, months, and so on. In some embodiments, such a regimen may be implemented for a patient with active caries, a history of caries, or considered at-risk for caries development. The amount, timing, and dosing of the compositions of the present disclosure can be determined for each patient by their dental health provider or by recommendation of a dental health association or guidelines.

Additional details regarding the tests and methods of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Characterization of the Arginolytic Microflora of Human Oral Biofilms

Introduction

The present example describes the isolation and characterization of arginolytic bacterial species from caries-free and caries-active subjects. A selected group of oral bacteria commonly associated with dental health is capable of producing alkali in the form of ammonia via the arginine deiminase system (ADS), which has a profound impact on the pH of human oral biofilms. An increased risk for dental caries has been associated with reduced ADS activity of the bacteria in oral biofilms. In this example, arginolytic bacterial strains from dental plaque samples of caries-free (CF) and caries-active (CA) adults were isolated and characterized to study the basis for differences in plaque ADS activity between individuals. Fifty ADS-positive bacterial strains were identified by 16S rRNA gene sequencing, and their ADS activity levels were compared under standard growth conditions. The spectrum of bacterial AD activity ranged from 45.2 to 688.0 units (mg protein)$^{-1}$. *Streptococcus sanguinis* was the most prevalent species/phylotypes. Biochemical assays carried out using 27 ADS-positive strains under conditions to induce or repress ADS gene expression showed variation in arginolytic activity in response to pH, oxygen, and the availability of carbohydrate or arginine. This study reveals that the basis for the wide spectrum of arginolytic expression observed among clinical isolates is, at least in part, attributable to differences in the regulation of expression of the ADS within and between species. The results provide insights into the microbiological basis for inter-subject differences in ADS capacity of oral biofilms and enhance our understanding of dental caries as an ecologically-driven disease in which arginine metabolism moderates plaque pH and promotes dental health and provides methods for identifying bacteria for probiotic compositions and uses.

Materials and Methods

Isolation of Bacterial Strains.

Supragingival dental plaque was collected from 11 caries-free (CF) subjects with no clinical or reported evidence of present or past caries experience [decayed, missing and filled teeth (DMFT)=0] and 3 caries-active (CA) subjects with at least four active, cavitated (dentin level) and unrestored caries lesions (DT≥4, MFT≥0) as described in Nascimento et al., (2009a) and Schulte et al., (2009). The activity of caries lesions was determined by clinical appearance, plaque stagnation, and tactile sensation. To acquire a variety of cultivable microflora, plaque samples were dispersed by external sonication (W375, Sonicator Heat Systems-Ultrasonics Inc, Farmingdale, N.Y., USA) for 2 cycles of 15 seconds, with cooling on ice during the interval. Samples were then serially diluted in 10 mM sodium phosphate buffer (pH 7.0), and 100 µl of the $10^{-4}$ to $10^{-7}$ diluted samples were cultured on Sheep Blood Agar plates (Columbia Agar containing 5% of anti-coagulated sheep blood, Difco Laboratories, Detroit, Mich., USA) and on Brain-Heart Infusion (BHI) Agar plates (Difco Laboratories, Detroit, Mich., USA). Plates were incubated at 37° C. in anaerobic jars (BBL GasPak™ Systems, BD, Sparks, Md., USA) for 3 days with subsequent aerobic incubation at 37° C. in 5% $CO_2$ for 2 days. After the incubation period, colonies of clinical isolates representing all morphological types were subcultured on the same media until pure colonies were obtained.

Screening of ADS-Positive Strains.

Bacterial strains were screened for the potential to liberate ammonia from arginine in a microtiter-based assay (Schulte et al., 2009). Briefly, strains were grown in clear polystyrene microtiter-plates (Fisher Scientific Inc., USA) containing tryptone-vitamin (TV)-based broth with 0.2% galactose and 10 mM arginine. The plates were incubated under anaerobic conditions (85% $N_2$, 5% $CO_2$, 10% $H_2$, 80% relative humidity) at 37° C. for 48 hours. Bacterial cells were collected by centrifuging the plates for 3 min at 10,000×g in a refrigerated microcentrifuge, washed once with 10 mM Tris-maleate (pH 7.0) and resuspended in 100 µl of 50 mM Tris-maleate buffer (pH 6.0). The ADS-positive phenotype was identified by detecting the ammonia generated from the incubation of bacteria in the presence of 50 mM arginine-HCl for 2 hours at 37° C. using the Nessler's reagent (Sigma-Aldrich Inc., USA) (FIG. 1). Controls for background and interference were routinely included in each reaction. The library of the ADS-positive strains was stored at −80° C. for further analysis. From this library, 56 ADS-positive strains were randomly selected from the plaque of the various CF and CA subjects to be identified by 16S rRNA gene sequencing and characterized in this study.
Amplification and Sequencing of 16S rRNA Genes by PCR.

Genomic DNA from ADS-positive bacteria was isolated using the QIAamp DNA mini kit (Qiagen Inc., CA, USA) according to the instructions of the supplier. The 16S rRNA genes were amplified under standardized conditions using a universal primer set (Forward: 5'-AGA GTT TGA TCC TGG CTC AG-3' (SEQ ID NO: 1), Reverse: 5'-TAC GGG TAC CTT GTT ACG ACT-3 (SEQ ID NO: 2)). Purified PCR-products of 16S rRNA inserts were sequenced using an ABI PCR conditions and the data analyzed as described in Aas et al., (2005); Paster et al., (2001). The PCR sequences were compared to the 16S rRNA sequences deposited at the Human Oral Microbiome Database (HOMD), Ribosomal Database Project, and the GenBank database. The complete 16S rRNA gene sequences generated in this study are available for electronic retrieval from the EMBL, GenBank, and DDBJ nucleotide sequence databases.
ADS Activity, Growth Conditions and Reagents.

To ensure that novel phylotypes and known bacterial species not previously reported as ADS-positive were, in fact, capable of metabolizing arginine, ADS activity of bacterial isolates was measured by monitoring citrulline production from arginine using protocols validated by Liu et al., (2008). Bacterial isolates were maintained on fresh cultures of BHI agar and inoculated on tryptone-yeast (TY) extract broth at 37° C. for 24 hours prior to the biochemical assays for determination of ADS activity. ADS activity of the 56 selected and identified ADS-positive strains was determined under the following standard growth condition: TY medium containing 25 mM galactose and 10 mM arginine at 5% $CO_2$, at 37° C. for 24 hours Liu et al., (2008). The concentration of protein was determined using a Pierce BCA protein assay kit (Waltham, Mass., USA) with bovine serum albumin served as the standard. ADS activity levels of bacterial isolates were normalized to protein content and defined as nmol of citrulline generated [minute×(mg protein)]$^{-1}$.

Figure 2A:
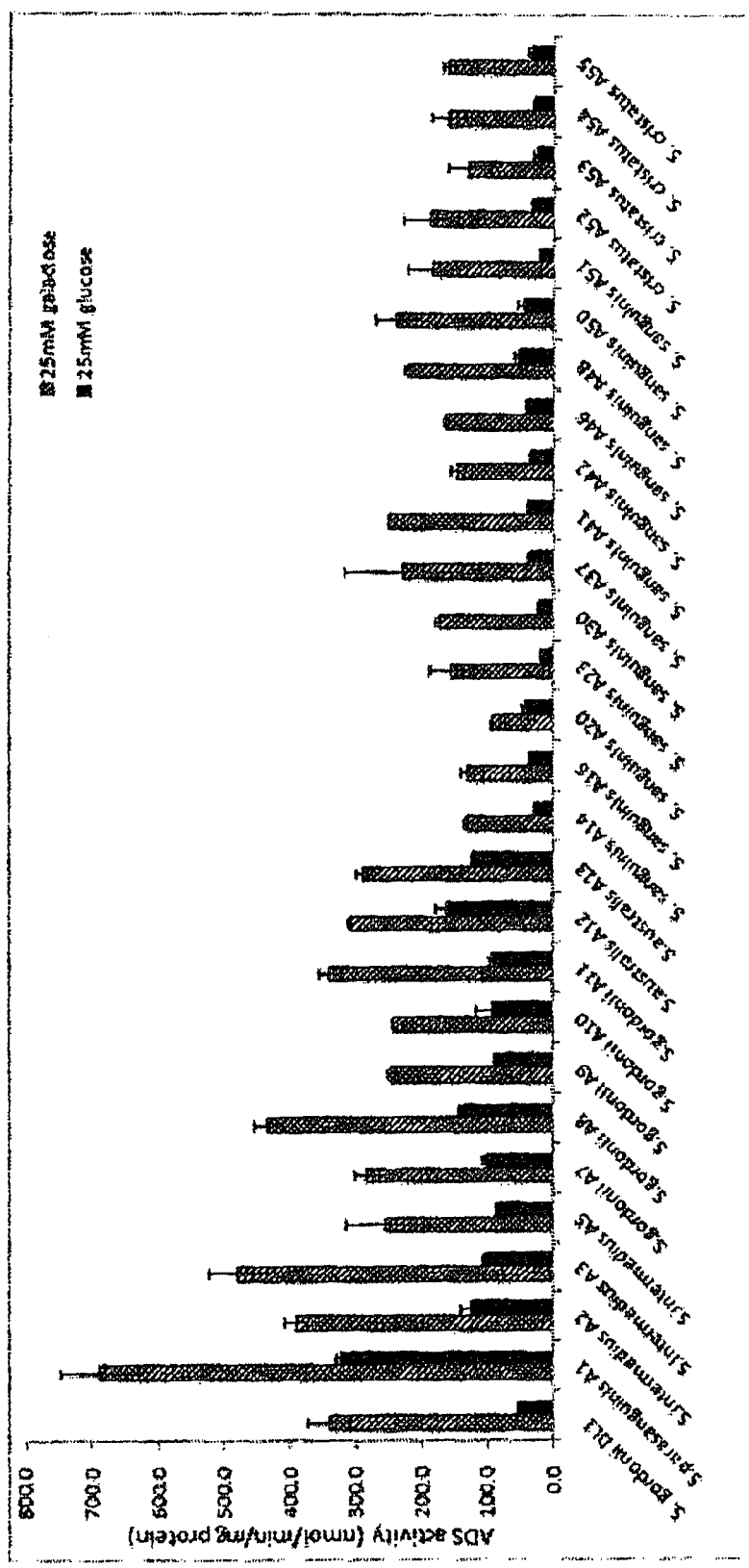
FIGS. 2A-2D represent a series of bar graphs illustrating the ADS activity levels of *S. gordonii* DL1 and ADS-positive isolates under different environmental conditions. The graphs illustrate the ADS activity in response to different sugars (FIG. 2A), different pH (FIG. 2B), the presence or absence of arginine (FIG. 2C), and aerobic (w/ $O_2$) or anaerobic (w/o $O_2$) conditions (FIG. 2D). Results represent the mean and standard deviations (error bars) of three independent experiments.
Figure 2B:
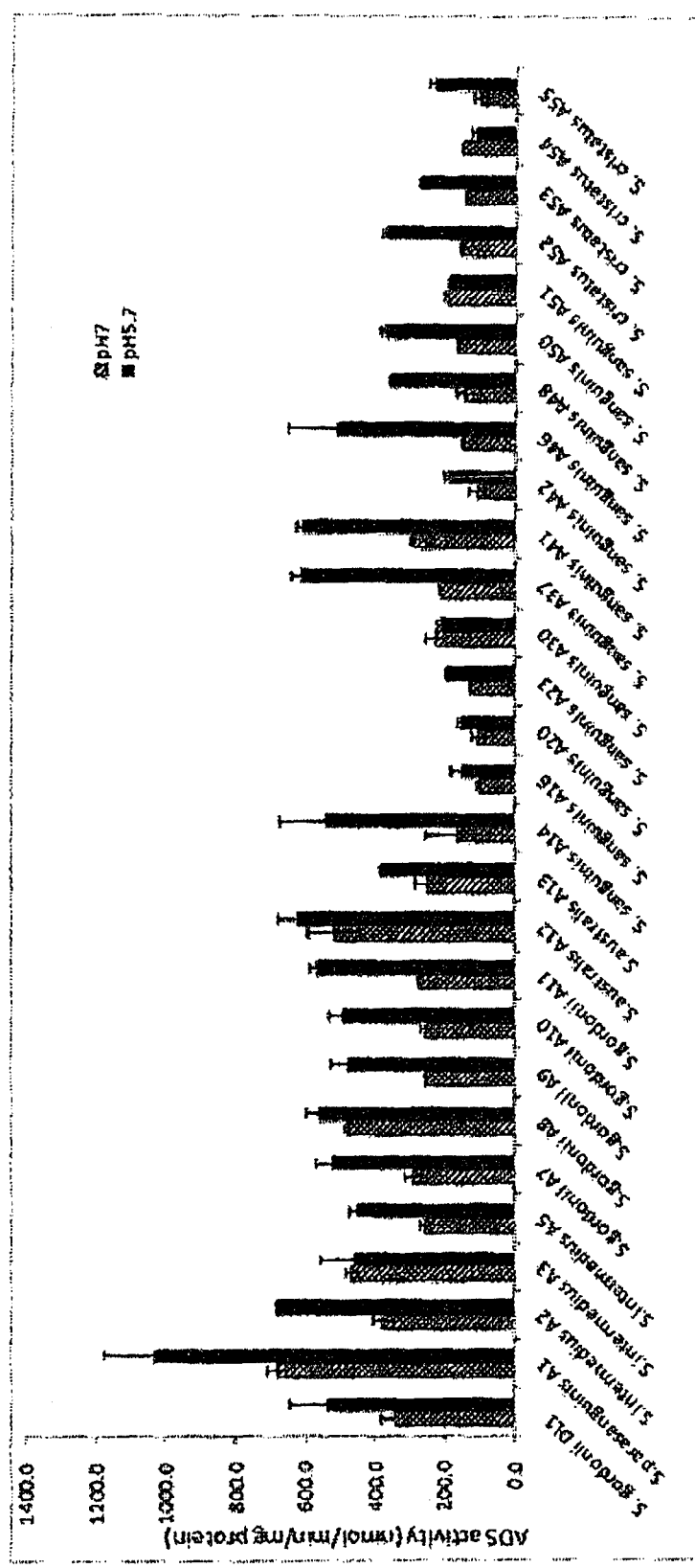
Figure 2C:
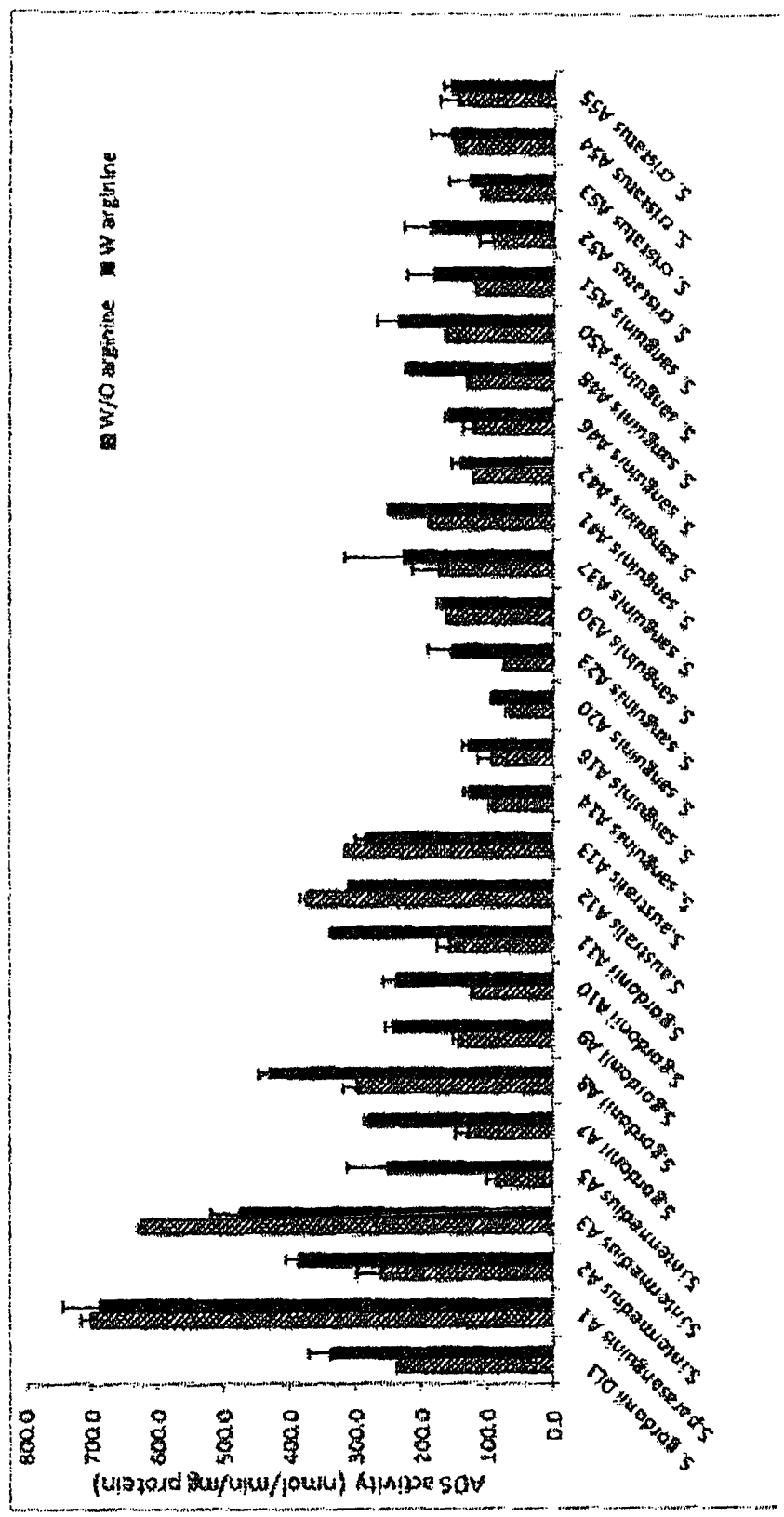

To monitor AD expression as a function of environmental conditions known to induce or repress the ADS, 27 representatives of different bacterial species were grown in TY base medium. For assays comparing ADS activity in response to different sugars, the base medium also contained 10 mM arginine and either 25 mM galactose or 25 mM glucose (FIGS. 2A and 3A). For the pH comparison assays (FIGS. 2B and 3B), the base medium also contained 25 mM galactose and 10 mM arginine that had been acidified to pH 5.7 with HCl or buffered at pH 7.0 with 50 MM $K_2HPO_4$—$KH_2PO_4$ buffer (TY/50 mM KPB). For the assays comparing the presence or absence of arginine (FIGS. 2C and 3C), the base medium also contained 25 mM galactose with or without 10 mM arginine. For the oxygen comparison assays (FIGS. 2D and 3D), the base medium also contained 25 mM galactose and 10 mM arginine with the cultures incubated under aerobic or anaerobic conditions. For aerobic growth, the cells were inoculated into a 250-ml conical flask containing 40 ml of TY medium supplemented with galactose and arginine and grown on a rotary shaker (50 rpm) at 37° C. (Liu and Burne, 2011). For anaerobic growth, cultures were incubated in an anaerobic chamber (85% $N_2$, 5% $CO_2$, 10% $H_2$, 80% relative humidity) at 37° C. for 24 hours. All the cells were collected at $OD_{600}$=0.5-0.6 for the detection of ADS activity.
Statistical Analysis.

For descriptive analysis, distribution of percentages and means were calculated when appropriate. Student's t-test or ANOVA were used to test the differences of continuous variables; and chi-square test was used for categorical variables. The correlation between the proportions of ADS-positive bacterial strains to the total cultivable organisms and the subjects' caries status was analyzed using the Two Proportions Z-test. The level of significance was determined at $p<0.05$.
Results
Arginolytic Bacterial Strains of Oral Biofilms.

A total of 2328 bacterial strains were isolated from plaque samples of the 14 participating subjects (11 CF and 3 CA; ratio of 166.3 strains isolated per subject) and screened for arginolytic capacity by detection of ADS activity. Of these 2328 strains, 288 were ADS-positive, which represents a ratio of 20.5 strains per subject, or 15.8 strains per CF subject (minimum of 5 ADS+ and maximum of 51 ADS+ strains within this caries group) and 38 strains per CA subject (minimum of 6 ADS+ and maximum of 84 ADS+ strains within this caries group). Despite considerable variation among the number of ADS-positive isolates identified within subjects and within the caries groups, there was a fair or unbiased distribution of the strains tested across subjects. There was no significant correlation between the proportions of ADS-positive strains in the total cultivable flora with the subjects' caries status.

Table 1 shows the diversity of arginolytic species isolated from supragingival dental plaque and identified by 16S rRNA gene sequencing. All 56 ADS-positive strains identified had greater than 99% sequence similarity with their assigned bacterial taxa. A total of 6 different bacterial taxa from the Firmicutes phyla were detected as the following: *S. sanguinis* (38%), *S. gordonii* (9%), *S. intermedius* (9%), *S. cristatus* (9%), *S. australis* (3%), and *S. parasanguinus* (2%).

TABLE 1

Identification and AD activities of ADS -positive isolates.

| SPECIES DESCRIPTION | STUDY CODE | ACCESSION NUMBER | SOURCE | ADS ACTIVITY (Mean ± SD) |
|---|---|---|---|---|
| *Streptococcus gordonii* DL1 | DL1 | | Lab strain | 339.3 ± 33.0 |
| arcA-deficient strains of *S. gordonii* | arcA- | | Lab strain | 0 |
| *S. parasanguinis* PTO10 | A1 | GU561390.1 | CF | 688.0 ± 57.1* |

TABLE 1-continued

Identification and AD activities of ADS-positive isolates.

| SPECIES DESCRIPTION | STUDY CODE | ACCESSION NUMBER | SOURCE | ADS ACTIVITY (Mean ± SD) |
|---|---|---|---|---|
| S. intermedius C270 *** | A2 | CP003858.1 | CF | 390.1 ± 17.3* |
| S. intermedius C270 *** | A3 | CP003858.1 | CF | 476.9 ± 43.8* |
| S. intermedius C270 *** | A4 | CP003858.1 | CF | 233.1 ± 15.7 |
| S. intermedius C270 *** | A5 | CP003858.1 | CF | 252.85 ± 61.79 |
| S. intermedius C270 *** | A6 | CP003858.1 | CF | 237.5 ± 11.5 |
| S. gordonii str. Challis substr. CH1 | A7 | AB690250.1 | CA | 283.3 ± 5.2 |
| S. gordonii str. Challis substr. CH1 | A8 | NR_074516.1 | CF | 431.9 ± 15.4* |
| S. gordonii ATCC 10558 | A9 | AY485606.1 | CA | 244.8 ± 10.7 |
| S. gordonii ATCC 10558 | A10 | AY485606.1 | CA | 241.3 ± 15.9 |
| S. gordonii ATCC 10558 | A11 | AY485606.1 | CF | 354.8 ± 20.9* |
| S. australis Al-1 | A12 | JX861483.1 | CF | 309.2 ± 1.4 |
| S. australis Al-1 | A13 | JX861483.1 | CF | 287.3 ± 12.7 |
| S. sanguinis SK36 | A14 | CP000387.1 | CF | 129.0 ± 5.6 |
| S. sanguinis SK36 | A15 | CP000387.1 | CF | 119.7 ± 3.7 |
| S. sanguinis SK36 | A16 | CP000387.1 | CF | 129.1 ± 10.4 |
| S. sanguinis SK36 | A17 | CP000387.1 | CF | 94.1 ± 4.3 |
| S. sanguinis SK36 | A18 | CP000387.1 | CF | 107.1 ± 9.1 |
| S. sanguinis SK36 | A19 | CP000387.1 | CF | 98.0 ± 5.7 |
| S. sanguinis SK36 | A20 | CP000387.1 | CF | 93.1 ± 1.4 |
| S. sanguinis SK36 | A21 | CP000387.1 | CF | 116.8 ± 14.0 |
| S. sanguinis SK36 | A22 | CP000387.1 | CF | 88.9 ± 10.0 |
| S. sanguinis SK1284_K2-1 | A23 | AB821291.1 | CA | 127.6 ± 1.1 |
| S. sanguinis JCM 5708 | A24 | AB596946.1 | CF | 45.2 ± 6.0 |
| S. sanguinis JCM 5708 | A25 | AB596946.1 | CF | 50.2 ± 3.4 |
| S. sanguinis JCM 5708 | A26 | AB596946.1 | CF | 46.0 ± 0.3 |
| S. sanguinis JCM 5708 | A27 | AB596946.1 | CF | 63.4 ± 0.0 |
| S. sanguinis JCM 5708 | A28 | AB596946.1 | CF | 56.4 ± 13.0 |
| S. sanguinis JCM 5708 | A29 | AB596946.1 | CF | 187.1 ± 20.3 |
| S. sanguinis JCM 5708 | A30 | AB596946.1 | CF | 173.3 ± 4.0 |
| S. sanguinis JCM 5708 | A31 | AB596946.1 | CF | 246.2 ± 2.4 |
| S. sanguinis JCM 5708 | A32 | AB596946.1 | CF | 227.3 ± 0.0 |
| S. sanguinis JCM 5708 | A33 | AB596946.1 | CF | 199.2 ± 8.3 |
| S. sanguinis JCM 5708 | A34 | AB596946.1 | CF | 200.6 ± 14.6 |
| S. sanguinis JCM 5708 | A35 | AB596946.1 | CF | 201.9 ± 15.2 |
| S. sanguinis JCM 5708 | A36 | AB596946.1 | CF | 263.4 ± 29.9 |
| S. sanguinis JCM 5708 | A37 | AB596946.1 | CF | 227.9 ± 89.7 |
| S. sanguinis JCM 5708 | A38 | AB596946.1 | CF | 167.7 ± 9.9 |
| S. sanguinis JCM 5708 | A39 | AB596946.1 | CF | 198.1 ± 5.1 |
| S. sanguinis JCM 5708 | A40 | AB596946.1 | CF | 212.5 ± 0.6 |
| S. sanguinis JCM 5708 | A41 | AB596946.1 | CF | 250.8 ± 1.3 |
| S. sanguinis JCM 5708 | A42 | AB596946.1 | CF | 144.0 ± 10.0 |
| S. sanguinis JCM 5708 | A43 | AB596946.1 | CF | 190.1 ± 10.6 |
| S. sanguinis JCM 5708 | A44 | AB596946.1 | CF | 106.4 ± 4.0 |
| S. sanguinis JCM 5708 | A45 | AB596946.1 | CF | 104.3 ± 4.1 |
| S. sanguinis JCM 5708 | A46 | AB596946.1 | CA | 161.3 ± 3.3 |
| S. sanguinis JCM 5708 | A47 | AB596946.1 | CA | 169.8 ± 6.4 |
| S. sanguinis JCM 5708 | A48 | AB596946.1 | CA | 221.3 ± 4.8 |
| S. sanguinis JCM 5708 | A49 | AB596946.1 | CA | 136.9 ± 4.3 |
| S. sanguinis JCM 5708 | A50 | AB596946.1 | CA | 238.2 ± 31.1 |
| S. sanguinis JCM 5708 | A51 | AB596946.1 | CA | 182.0 ± 39.3 |
| S. cristatus ATCC 51100 | A52 | AY584476.1 | CA | 187.5 ± 41.4 |
| S. cristatus ATCC 51100 | A53 | AY584476.1 | CA | 129.2 ± 31.6 |
| S. cristatus F0329 | A54 | AY005047.1 | CA | 160.0 ± 26.2 |
| S. cristatus F0329 | A55 | AY005047.1 | CA | 159.0 ± 9.1 |
| S. cristatus F0329 | A56 | AY005047.1 | CA | 185.9 ± 41.8 |

The 56 ADS-positive strains identified had greater than 99% sequence similarity with their assigned bacterial taxa.
Database accession numbers are provided.
(⁺) Human Oral Taxon ID (HOT) from the Human Oral Microbiome Database (HOMD);
*ADS activity levels of bacterial strains are higher than that of S. gordonii DL1; ADS activity was expressed as nmol of citrulline generated [minute × (mg of protein)]$^{-1}$;
CF: caries-free and CA: caries-active subjects;
SD: standard deviation.

The spectrum of bacterial AD activity ranged from 45.2 to 688.0 units (mg protein)$^{-1}$ when bacterial cells were incubated under standard growth conditions. There was no statistical difference between the average of bacterial ADS activity among the caries groups.

ADS Expression as a Function of Environmental Stimuli.

To examine regulation of ADS activity in high expressers, AD enzyme activity was measured under growth conditions known to affect the expression of ADS genes in oral bacteria, including low pH, availability of oxygen, arginine and carbohydrate. A substantial variation in ADS expression patterns was observed in response to pH, oxygen, and the availability of arginine and carbohydrate as illustrated in FIGS. 2 and 3. FIG. 2C shows that for most strains, including the laboratory strain S. gordonii DL1, optimal expression of ADS was strongly dependent on the presence of arginine. However, strains such as *S. parasanguinis* A1, *S. intermedius* A2, *S. intermedius* A3, *S. gordonii* A8, *S. australis* A12, and *S. australis* A13 demonstrated higher ADS expression compared to *S. gordonii* DL1, even in the absence of arginine. Also of note, the availability of arginine had no apparent effect on ADS expression of strains presenting lower ADS activity levels, which included *S. sanguinis* A14, *S. sanguinis* A16, and *S. sanguinis* A20.

A low pH environment is known to enhance ADS activity in *S. gordonii* DL1, however, *S. parasanguinis* A1, *S. intermedius* A2, *S. intermedius* A3, *S. gordonii* A8, and *S. australis* A12 were capable of expressing high levels of ADS activity even when cells were cultured at neutral pH (FIG. 2B), with lower fold-induction levels observed at pH 5.7.

The ADS activity of *S. gordonii* DL1 is also very sensitive to CCR (Dong et al., 2004), with growth in glucose resulting in 5-fold lower ADS activity compared to cells cultivated in galactose (Dong et al., 2004), which is less effective at eliciting CCR than glucose. Similarly, glucose could lower ADS activity by 8- to 10-fold in many ADS-positive strains when compared to growth in galactose (FIG. 2A). Yet, no observable repression of ADS activity by glucose was detected in *S. parasanguinis* A1, *S. intermedius* A2, *S. intermedius* A3, *S. intermedius* A5, *S. gordonii* A7, *S. gordonii* A8, *S. gordonii* A9, *S. gordonii* A10, *S. gordonii* A11, *S. australis* A12, and *S. australis* A13.

Figure 2D:
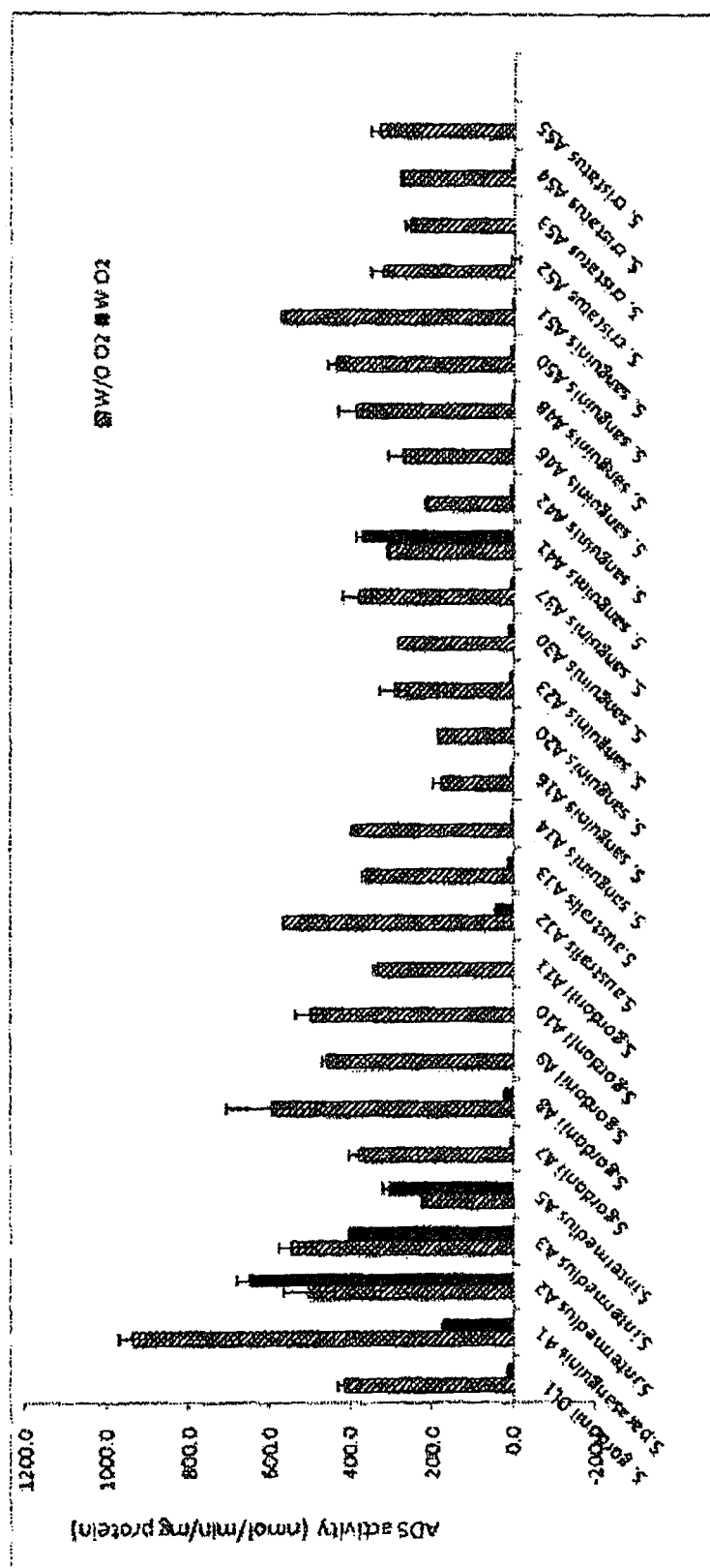

FIG. 2D shows that ADS expression of *S. gordonii* DL1 was highly repressed by growth under aerobic conditions and similar repression by oxygen was observed in other clinical strains. However, the ADS activity levels of some strains, such as *S. parasanguinis* A1, *S. intermedius* A2, *S. intermedius* A3, *S. intermedius* A5, *S. gordonii* A8, *S. australis* A12, *S. sanguinis* A41, and *S. cristatus* A55, were insensitive to the repressive effects of growth in aerated conditions.

ADS Expression and Caries Status.

As shown in Table 1, different levels of ADS activity were observed among strains of the same species isolated from plaque of CF and CA subjects. For example, the strains *S. sanguinis* A24 [45.2 units (mg protein)$^{-1}$] from a CF subject and A48 [221.3 units (mg protein)$^{-1}$] from a CA subject presented considerably different ADS expression under standard growth conditions. To further explore whether the arginolytic capacity of oral bacteria was related to the subjects' caries status, ADS expression in response to different environmental conditions was compared for clinical strains of same species isolated from the different caries groups (FIG. 3). The selected strains included those with highest 16S rRNA sequence similarity to *S. gordonii* Challis substr. CH1 (A7 and A8), *S. gordonii* ATCC 10558 (A10 and A11), *S. sanguinis* JCM 5708 (A37, A41, A48 and A50).

Figure 3B:
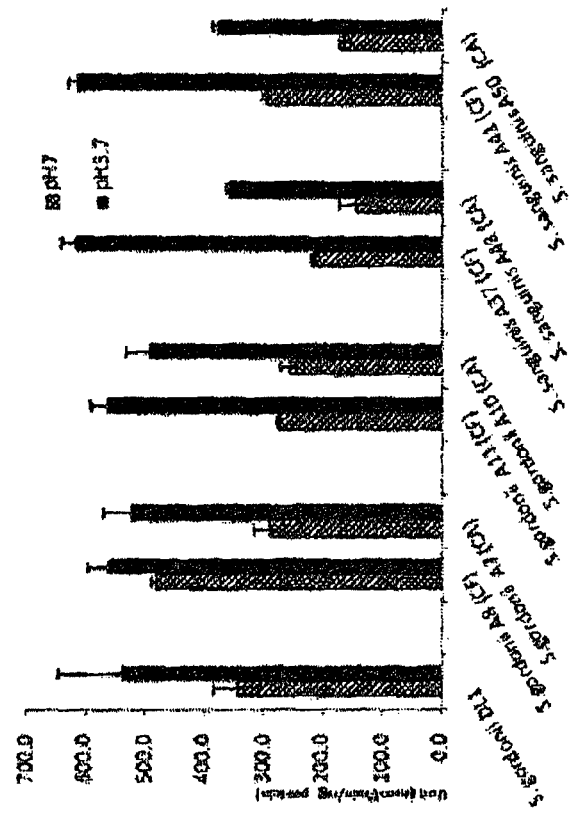
Figure 3A:
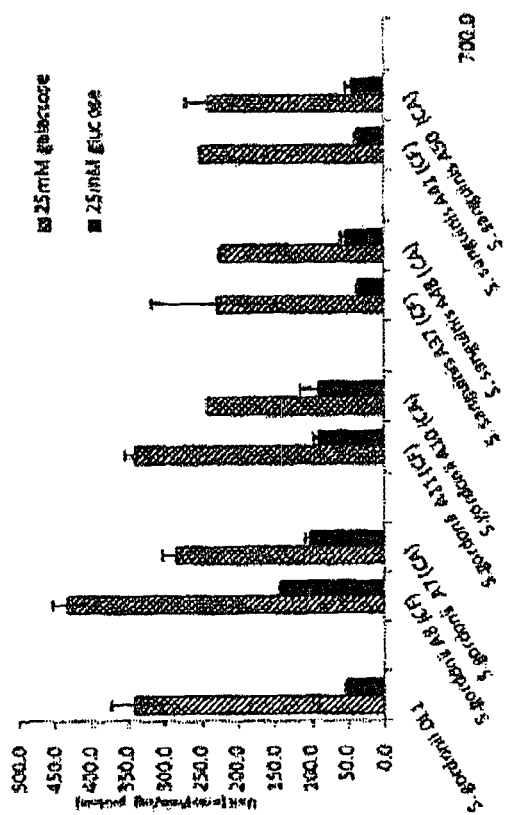
Figure 4B:
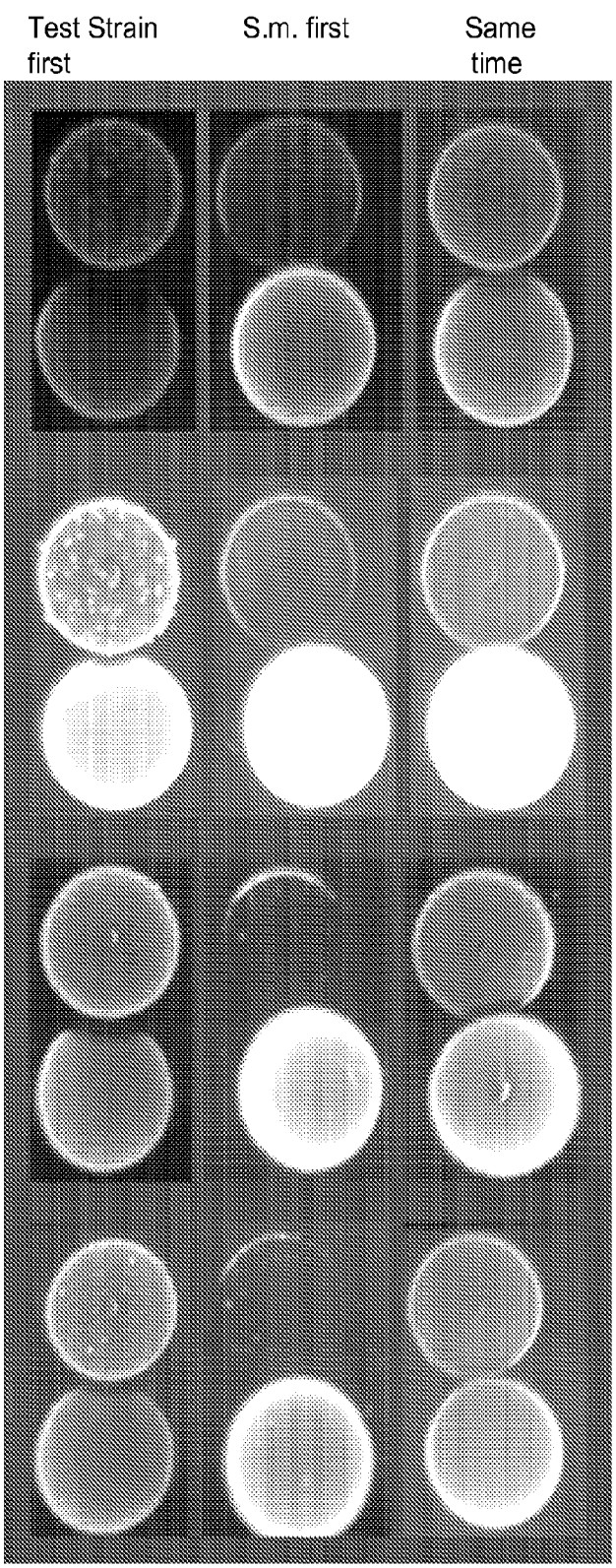
Figure 4C:
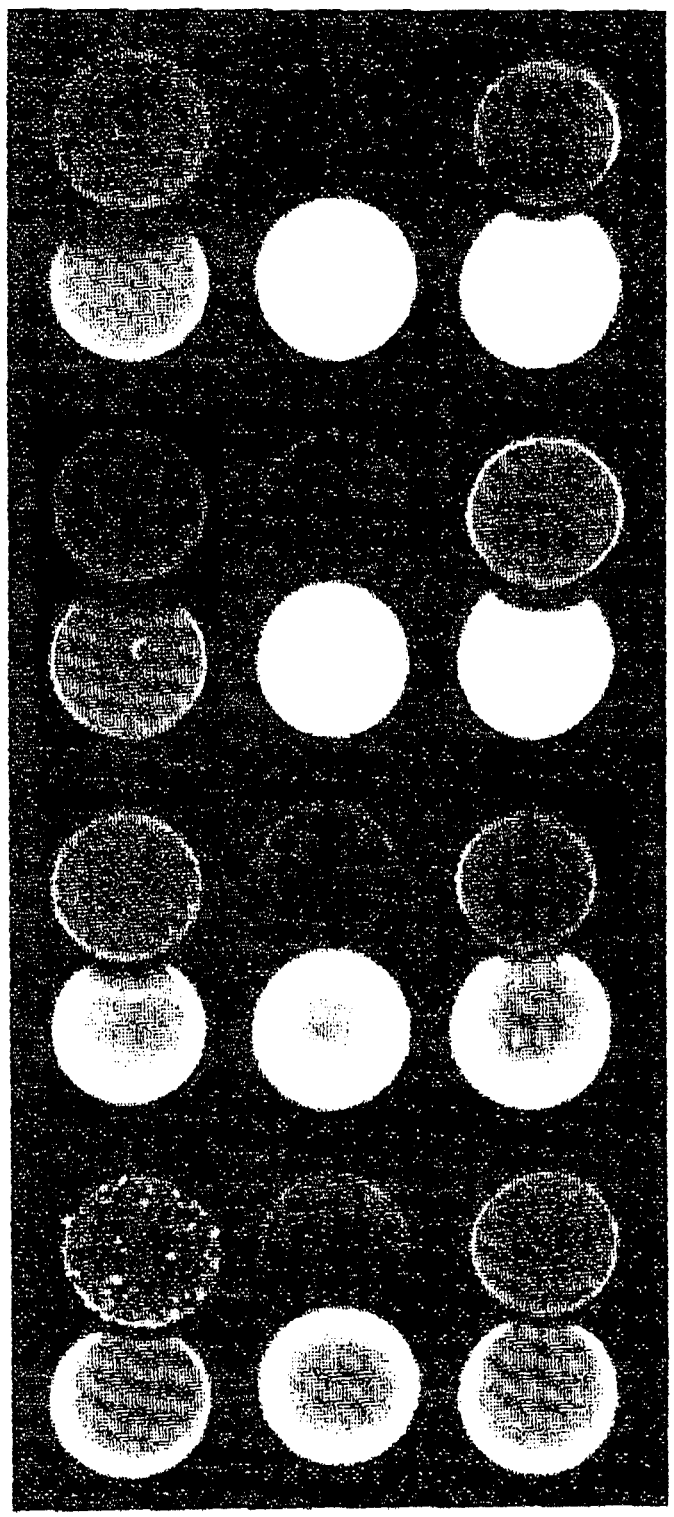
Figure 4D:
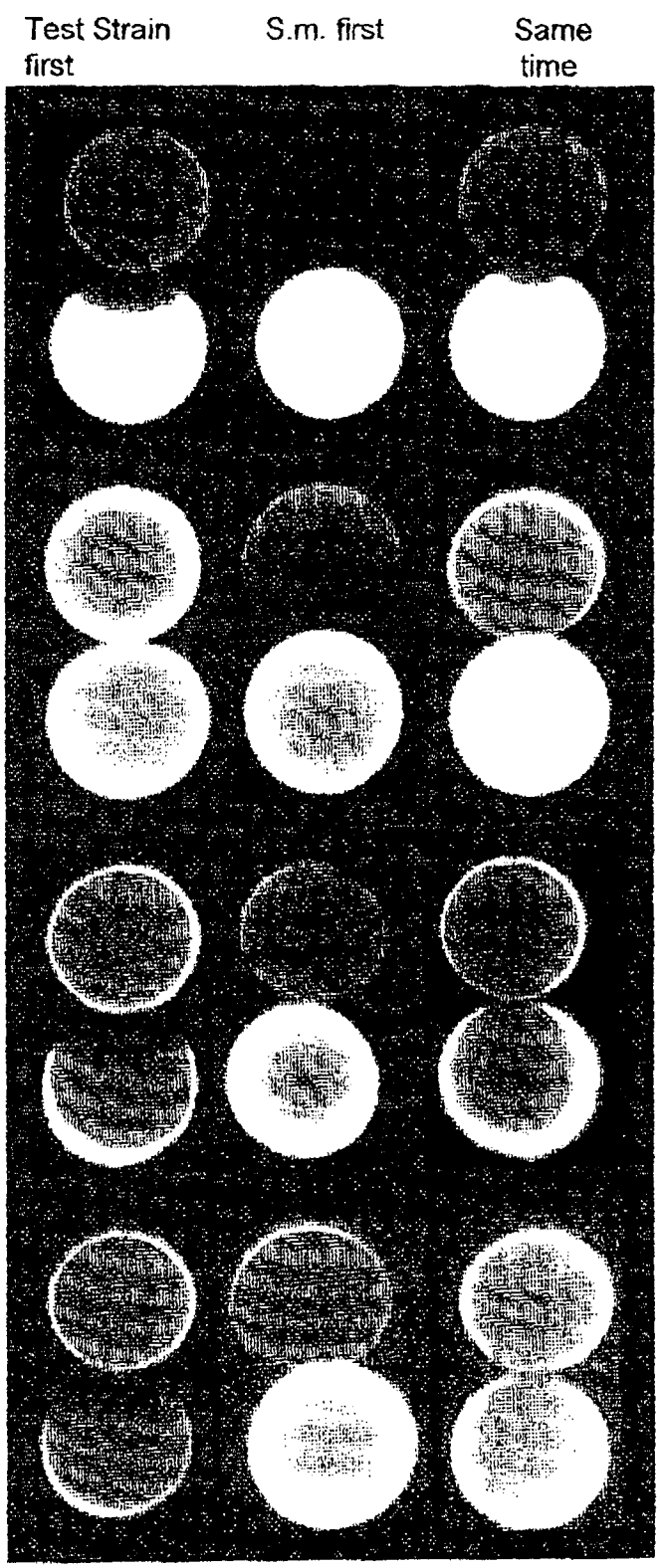

The strains of *S. gordonii* and *S. sanguinis* strains showed similar repression of ADS expression by glucose (FIG. 3A). Similar patterns for ADS expression and induction by acidic pH were also observed among the strains of *S. gordonii* and *S. sanguinis* from both caries (FIG. 3B). FIG. 3C shows that most strains of the same species presented comparable differences in ADS expression in response to arginine independently of the subjects' caries status. For example, both *S. gordonii* A7 from a CA subject and *S. gordonii* A8 from a CF subject showed 2-fold higher ADS activity in the presence of arginine compared to growth in the absence of arginine. Most strains showed repression of the ADS by oxygen (FIG. 3D); except for *S. sanguinis* A41 of a CF subject.

Discussion

Arginine metabolism in oral biofilms offers the opportunity for the development of novel anti-caries approaches from the standpoint of its short-term moderation of acid challenges to teeth and long-term effects on the persistence of desirable bacteria in dental plaque. For arginolysis is to be used in the development of strategies to assess caries risk and to control caries, insight into the distribution, regulation and function of the ADS in oral biofilms in health and disease was needed. Although genome sequencing and other molecular techniques have revealed new levels of complexity in the cariogenic microflora and in the nature of individual bacterial species (Aas et al., 2008; Corby et al., 2005; Crielaard et al., 2011; Mager et al., 2003; Russell, 2008), limited attempts (Sissons et al., 1988a; Sissons et al., 1988b; Sissons et al., 1994) have been made to identify and characterize clinically-relevant oral organisms capable of producing alkali that can potentially affect the cariogenicity of oral biofilms. In this example, a rapid and simple protocol was developed for screening of cultivable arginolytic bacteria isolated from dental plaque samples. Even though the majority of the ADS-positive bacterial species identified were strains of *S. sanguinis* and *S. gordonii*, we were able to disclose additional cultivable taxa that contribute to the total oral arginolysis, such as species of *Actinomyces, Bacillus*, and *Neisseria*. In conjunction with previous microbiological studies demonstrating the abundance in human oral biofilms of the commensal streptococci identified here (Aas et al., 2008; Aas et al., 2005; Corby et al., 2005; Crielaard et al., 2011; Dewhirst et al., 2010; Gross et al., 2010; Mager et al., 2003), the results in these examples revealed that these abundant streptococci likely have a dominant influence on the arginolytic capacity of human oral biofilms. Importantly, this study clearly demonstrated that the ADS of clinical strains is in fact regulated in response to those specific environmental factors that have the greatest impact on the composition and biochemical activities of supragingival biofilms; e.g. availability and source of carbohydrate, low pH and oxygen, which are also environmental factors that can influence the development of caries.

The diversity of the oral microbiota associated with health and disease is only beginning to be described by high-throughput methodologies (Aas et al., 2008; Corby et al., 2005; Crielaard et al., 2011; Gross et al., 2010; Mager et al., 2003). While this species- or taxa-level identification is tremendously valuable (Dewhirst et al., 2010), it does not address the fact that there is significant heterogeneity within given species of oral bacteria. Based on current sequencing efforts, the majority of ADS-positive oral bacterial species is cultivable, and mostly includes abundant oral streptococci. Uncultivable organisms may also contribute to the total arginolytic activity measured in oral biofilms. However, this theory is not supported by the above results, in which there was no association of alkali-generating potential with organisms that were unlikely to grow under the conditions used in the present examples to cultivate plaque samples or that are generally recognized as uncultivable, e.g. certain spirochetes. Thus, any contribution to total ADS of uncultivable organisms is probably negligible. Not only are uncultivable bacterial species represented in plaque in far lower amounts compared to cultivable species (Aas et al., 2008; Corby et al., 2005; Crielaard et al., 2011; Gross et al., 2010; Mager et al., 2003), but many or most of the uncultivable bacteria do not appear to harbor the ADS genes. This present study enhances ongoing oral microbiome efforts by highlighting the phenotypic heterogeneity of the more abundant species in the oral cavity in the context of their abilities to modulate the pH, and thus the cariogenic potential, of oral biofilms. This study also presents novel concepts regarding the molecular basis for heterogeneity in alkali production, while concurrently generating knowledge, strains, probes and reagents that will advance existing methodologies for evaluating and understanding the pathogenic potential of the oral microbiome.

Markedly less is known about the production of alkali than is known about sugar metabolism in oral biofilms. The causal relationship between bacterial sugar metabolism and acid production by a mixed population of plaque bacteria was first described by Stephan in 1940 (Stephan, 1940). Stephan also pointed out that the drop in plaque pH detected after sugar challenge is followed by a gradual rise in plaque pH that eventually reaches a plateau. Later, the plateau, or resting pH, of caries-active plaque was found to be more acidic than that of caries-free plaque (Margolis et al., 1988a), further supporting a correlation between acid production and dental caries. Subsequent studies showed that the rise in plaque pH is largely due to ammonia production from arginine or urea by a subset of acid-sensitive organisms present in saliva and plaque (Wijeyeweera and Kleinberg, 1989b). Marquis suggested that the buffering capacity from ammonia production in oral biofilms moderates the speed of the pH drop and allows time for the base-producing bacteria to adjust their physiology for survival (Marquis, 1995). Kleinberg showed that carbohydrate-starved plaque was more alkaline than the saliva bathing the plaque, mainly in regions of greater saliva flow (Kleinberg and Jenkins, 1964), so it was suggested that plaque bacteria generate ammonia from salivary substrates more rapidly than the forces of diffusion can clear them from dental plaque (Kleinberg and Jenkins, 1964). Kleinberg also indicated that the plaque pH would be determined by the acid-base metabolism of plaque organisms, which in turn could be affected by plaque thickness, the proportions of acid- and base-producing organisms in plaque, and the relative availability of nitrogenous and carbohydrates substrates (Kleinberg, 1970).

Clinical studies to date support that caries susceptibility involves a deficiency in alkali production and not solely acid production, as has been traditionally assumed (Nascimento et al., 2009b; Nascimento et al., 2012; Shu et al., 2007b). In the present example, we examined whether the heterogeneity of oral bacterial strains, the constitutional difference in the ADS genes expression levels, and/or differential sensitivity of the ADS genes to induction or repression by environmental factors, could account for the high degree of variability in alkali production detected in dental health and when caries activity is evident. Although ADS-positive strains from caries-free subjects showed slightly higher levels of ADS activity than those isolated from caries-active subjects, there was no significant correlation between levels of bacterial ADS activity and hosts' caries status. Yet, this study examining a collection of arginolytic plaque bacteria, or more specifically, the ADS activity in closely-related but physiologically-diverse commensal streptococci, revealed a considerable and surprising spectrum of responses of the ADS to multiple environmental stimuli. In the complex environment of oral biofilms where many variables can influence microbial behavior, the arginolytic expression of clinical strains may be dependent on the growth conditions. Thus, it is possible that the basis for differences in arginolysis observed between caries-free and caries-active subjects can be associated with a combination of factors: (i) the carriage in oral biofilms of strains that have inherent differences in the regulation of the ADS by environmental factors, and/or (ii) host and biofilm micro-environmental factors that influence ADS expression in vivo. For example, the biofilms of caries-active subjects appear to be in-conducive to high ADS expression or to provide some inhibitory factors that decrease ADS activity. Thus, arginolytic clinical strains with constitutionally high ADS-expressing phenotypes and those in which ADS expression is insensitive to conditions known to cause dental caries, such as sugar availability and acidic environment, have use in probiotic therapies to prevent and control dental caries.

This study reveals that the microbial basis for intra-subject variations in oral arginolysis is more complex than previously appreciated; not only may the arginolytic potential of oral biofilms be associated with the carriage of certain strains of bacteria, but also arginolytic species display a range of ADS activity as a function of environmental factors. The results are highly significant in the context of understanding caries as an ecologically-driven disease by supporting that high ADS-expressing strains could positively affect plaque ecology synergistically by moderating plaque pH and reducing the risk for caries. This study expanded the knowledge on the diversity of the oral alkali-generating bacteria and their role in oral health and disease.

Example 2

ADS Activity and Interspecies Antagonism

Introduction

The present example describes the determination of whether antagonistic interactions of arginolytic isolates toward *Streptococcus mutans* can be correlated with arginolytic potential.

Methods and Materials

Clinical Isolation and Screening.

Samples were obtained and plated as described above for Example 1.

Bacterial Strains, Growth Conditions and Reagents.

Bacterial strains were maintained as described above for Example 1.

16S rDNA Sequencing and Biochemical Assays.

Sequencing and assays were as described above for Example 1.

Interspecies Antagonism.

To examine the antagonistic interactions of arginolytic isolates toward the cariogenic bacteria *Streptococcus mutans*, overnight cultures of *S. mutans* and ADS-positive isolates in BHI broth medium were adjusted to the same optical density (OD600=0.5). Then, 6 µl aliquots of *S. mutans* and ADS-positive isolates were inoculated adjacent to one another on TY-25 mM galactose agar plates as follows: (i) ADS-positive isolates were inoculated first, followed by inoculation of *S. mutans* 24 h later; (ii) *S. mutans* was inoculated first, followed by inoculation of ADS-positive isolates 24 h later, and (iii) ADS-positive isolates and *S. mutans* were inoculated simultaneously. The plates were cultured for another 24 h during which the interaction was monitored. The bacteria were grown at 37° C. with 5% CO2 and 95% air. AlphaEaseFC software was used to measure zones of growth inhibition.

Results

Interspecies Antagonism.

To study the correlation of ADS activity with interspecies antagonism, antagonism of and by *S. mutans* UA159 with different ADS activities isolates were examined using plate inhibition assays (Table 2). Highly ADS-active isolates showed the ability to survive in the presence of *S. mutans*. As importantly, isolates of *S. gordonii*, *S. australis* and *S.* sanguinis showed a potent ability to inhibit the growth of S. mutans UA159 (Table 2 and FIGS. 4A-4D). Also of note, the growth of many of the ADS-positive isolates was not inhibited by S. mutans (FIGS. 4A-4D). Thus, not only may the arginolytic potential of oral biofilms be associated with the carriage of certain strains of bacteria, but also arginolytic species display a range of abilities to inhibit, and to be inhibited by, S. mutans.

TABLE 2

Inhibitory effects of ADS-positive isolates on the growth S. mutans UA159.

| | | Antagonistic activity (on TY-galactose medium) | | |
|---|---|---|---|---|
| SPECIES DESCRIPTION | STUDY CODE | Testing strain first (unit: 0.1 mm) | S. mutans first (unit: 0.1 mm) | At the same time (unit: 0.1 mm) |
| Streptococcus gordonii DL1 | | 7.2 ± 0.4 | −64.8 ± 2.2 | 6.8 ± 0.8 |
| arcA-deficient strains of S. gordonii | | 7.2 ± 0.4 | −62.0 ± 2.2 | 5.0 ± 0.8 |
| S. parasanguinis PTO10 | A1 | 5.0 ± 0 | 0 ± 0 | 0 ± 0 |
| S. intermedius C270 *** | A2 | 0 ± 0 | −80.0 ± 0 | −25.0 ± 1.4 |
| S. intermedius C270 *** | A3 | 0 ± 0 | −80.0 ± 0 | −32.3 ± 3.1 |
| S. intermedius C270 *** | A4 | 0 ± 0 | −80 ± 0 | −39.4 ± 2.6 |
| S. intermedius C270 *** | A5 | 0 ± 0 | −80 ± 0 | −57.3 ± 2.8 |
| S. intermedius C270 *** | A6 | 0 ± 0 | −80 ± 0 | −55.0 ± 3.0 |
| S. gordonii str. Challis substr. CH1 | A7 | 6.0 ± 0.7 | −70.0 ± 0 | 3.0 ± 0.8 |
| S. gordonii str. Challis substr. CH1 | A8 | 22.8 ± 2.2** | −18.3 ± 2.1 | 13.0 ± 0.8 |
| S. gordonii ATCC 10558 | A9 | 5.8 ± 0.4 | −66.8 ± 2.4 | 5.2 ± 0.8 |
| S. gordonii ATCC 10558 | A10 | 4.6 ± 0.5 | −71.8 ± 9.5 | 4.4 ± 0.5 |
| S. gordonii ATCC 10558 | A11 | 12.5 ± 1.8** | −40.0 ± 0 | 3.0 ± 1.2 |
| S. australis Al-1 | A12 | 20.6 ± 1.3** | −65.0 ± 6.0 | 8.6 ± 0.9 |
| S. australis Al-1 | A13 | 22.4 ± 3.6** | −63.7 ± 3.8 | 7.2 ± 0.8 |
| S. sanguinis SK36 | A14 | 12.7 ± 1.6** | −80.0 ± 0 | 6.4 ± 3.1 |
| S. sanguinis SK36 | A15 | 11.4 ± 1.1** | −80 | 2.8 ± 0.8 |
| S. sanguinis SK36 | A16 | 18.5 ± 2.4** | −25.3 ± 4.5 | 9.6 ± 1.1 |
| S. sanguinis SK36 | A17 | 21.0 ± 2.0** | 0 ± 0 | 12.5 ± 1.0 |
| S. sanguinis SK36 | A18 | 14.3 ± 1.7** | 0 ± 0 | 7.0 ± 1.0 |
| S. sanguinis SK36 | A19 | 17.8 ± 1.0** | −29.5 ± 4.5 | 13.4 ± 1.5 |
| S. sanguinis SK36 | A20 | 14.5 ± 0.6** | −80 ± 0 | 4.8 ± 0.5 |
| S. sanguinis SK36 | A21 | 13.0 ± 1.1** | −64.3 ± 3.1 | 5.2 ± 0.8 |
| S. sanguinis SK36 | A22 | 6.0 ± 1.7 | −73.3 ± 5.2 | 4.0 ± 1.0 |
| S. sanguinis SK1284_K2-1 | A23 | 7.0 ± 0.9** | −75 ± 5.8 | 4 ± 1.2 |
| S. sanguinis JCM 5708 | A24 | 4.6 ± 0.9 | −80.0 ± 0 | −15.0 ± 4.0 |
| S. sanguinis JCM 5708 | A25 | 0 ± 0 | −80.0 ± 0 | −7.25 ± 0.5 |
| S. sanguinis JCM 5708 | A26 | 5.6 ± 1.7 | −80.0 ± 0 | 1.6 ± 0.9 |
| S. sanguinis JCM 5708 | A27 | 0 ± 0 | −80 ± 0 | 0.2 ± 2.4 |
| S. sanguinis JCM 5708 | A28 | 2.0 ± 0 | −65.8 ± 2.9 | 2.0 ± 0 |
| S. sanguinis JCM 5708 | A29 | 2.4 ± 0.9 | −80.0 ± 0 | 0 ± 0 |
| S. sanguinis JCM 5708 | A30 | 6.3 ± 0.5 | −80.0 ± 0 | 0 ± 0 |
| S. sanguinis JCM 5708 | A31 | 2.6 ± 0.5 | −76.7 ± 5.8 | −14.6 ± 3.2 |
| S. sanguinis JCM 5708 | A32 | 4.2 ± 0.8 | −70.0 ± 5.3 | 0 ± 0 |
| S. sanguinis JCM 5708 | A33 | 20.4 ± 1.1** | −61.5 ± 3.0 | 6.8 ± 1.3 |
| S. sanguinis JCM 5708 | A34 | 9.8 ± 0.4** | −71.75 ± 2.6 | 1.8 ± 0.5 |
| S. sanguinis JCM 5708 | A35 | 9.0 ± 0.9** | −69.5 ± 1.9 | 4.0 ± 1.2 |
| S. sanguinis JCM 5708 | A36 | 1.0 ± 0 | −66.5 ± 1.0 | 2.0 ± 0 |
| S. sanguinis JCM 5708 | A37 | 5.6 ± 1.7 | −68.5 ± 3.7 | 1.0 ± 0.7 |
| S. sanguinis JCM 5708 | A38 | 3.6 ± 0.9 | −68.5 ± 2.5 | −5.8 ± 1.7 |
| S. sanguinis JCM 5708 | A39 | 6.8 ± 0.8 | −63.3 ± 7.2 | 2.5 ± 1.3 |
| S. sanguinis JCM 5708 | A40 | 1.8 ± 0.8 | −61.8 ± 2.8 | 1.6 ± 0.5 |
| S. sanguinis JCM 5708 | A41 | 0 ± 0 | −80 ± 0 | −9 ± 3.3 |
| S. sanguinis JCM 5708 | A42 | 11.6 ± 2.1** | −29.0 ± 1.0 | 9.4 ± 0.5 |
| S. sanguinis JCM 5708 | A43 | 12.8 ± 1.7** | −68.0 ± 3.5 | 14.7 ± 1.4 |
| S. sanguinis JCM 5708 | A44 | 5.8 ± 0.5 | −43.8 ± 4.8 | 3.8 ± 1.1 |
| S. sanguinis JCM 5708 | A45 | 8.0 ± 1.2** | −80 ± 0 | 8.5 ± 1.0 |
| S. sanguinis JCM 5708 | A46 | 0.7 ± 1.0 | −80 ± 0 | 0.7 ± 1.0 |
| S. sanguinis JCM 5708 | A47 | 2.58 ± 2.4 | −80.0 ± 0 | 0.68 ± 0.9 |
| S. sanguinis JCM 5708 | A48 | 0.4 ± 0.9 | −80.0 ± 0 | 0 ± 0 |
| S. sanguinis JCM 5708 | A49 | 5.8 ± 0.5 | 0 | 6.6 ± 0.5 |
| S. sanguinis JCM 5708 | A50 | 0 ± 0 | −69.2 ± 2.0 | 0 ± 0 |
| S. sanguinis JCM 5708 | A51 | 5.2 ± 0.4 | 2.0 ± 0 | 4.7 ± 1.5 |
| S. cristatus ATCC 51100 | A52 | 16.0 ± 1.3** | −80.0 ± 0 | −19.0 ± 5.3 |
| S. cristatus ATCC 51100 | A53 | 4.8 ± 1.2 | −80.0 ± 0 | 1.8 ± 0.5 |
| S. cristatus F0329 | A54 | 1.5 ± 1.0 | −80.0 ± 0 | 1.3 ± 0.5 |
| S. cristatus F0329 | A55 | 16.5 ± 0.5** | −80.0 ± 0 | 4.0 ± 0.8 |
| S. cristatus F0329 | A56 | 5.6 ± 2.1 | −80.0 ± 0 | −19.3 ± 5.1 |

**Antagonistic activity levels of bacterial strains are higher than that of S. gordonii DL1 when arginolytic isolate were inoculated first (before the S. mutans strain); (−) Arginolytic isolates were inhibited by S. mutans; SD: standard deviation.

CONCLUSION

This study revealed that dental biofilms are colonized by a diverse arginolytic community and that the basis for variation in ADS expression between subjects is likely, in large part, due to intra-strain variability in the regulation of the ADS. Collectively, the results support that strains expressing high levels of the ADS could have positive and synergistic effects on plaque ecology by moderating plaque pH and directly antagonizing the growth of known caries pathogens.

REFERENCES

The following references are incorporated herein by reference in pertinent part.

Aas J A, Griffen A L, Dardis S R, Lee A M, Olsen I, Dewhirst F E, Leys E J, Paster B J: Bacteria of dental caries in primary and permanent teeth in children and young adults. J Clin Microbiol 2008; 46:1407-1417.

Aas J A, Paster B J, Stokes L N, Olsen I, Dewhirst F E: Defining the normal bacterial flora of the oral cavity. J Clin Microbiol 2005; 43:5721-5732.

Becker M R, Paster B J, Leys E J, Moeschberger M L, Kenyon S G, Galvin J L, Boches S K, Dewhirst F E, Griffen A L: Molecular analysis of bacterial species associated with childhood caries. J Clin Microbiol 2002; 40:1001-1009.

Burne R, Liu, Y, Zeng, L: Acid tolerance strategies of commensal and pathogenic oral streptococci.; in: Society for General Microbiology Autumn 2010 Meeting. Nottingham, UK, 2010.

Burne R A, Marquis R E: Alkali production by oral bacteria and protection against dental caries. FEMS Microbiol Lett 2000a; 193:1-6.

Burne R A, Marquis R E: Alkali production by oral bacteria and protection against dental caries. FEMS Microbiol Lett 2000b; 193:1-6.

Burne R A, Parsons, D. T. and Marquis, R. E.: Environmental variables affecting arginine deiminase expression in oral streptococci. Washington, D.C., 1991.

Casiano-Colon A, Marquis R E: Role of the arginine deiminase system in protecting oral bacteria and an enzymatic basis for acid tolerance. Appl Environ Microbiol 1988; 54:1318-1324.

Clancy K A, Pearson S, Bowen W H, Burne R A: Characterization of recombinant, ureolytic streptococcus mutans demonstrates an inverse relationship between dental plaque ureolytic capacity and cariogenicity. Infection and immunity 2000; 68:2621-2629.

Corby P M, Lyons-Weiler J, Bretz W A, Hart T C, Aas J A, Boumenna T, Goss J, Corby A L, Junior H M, Weyant R J, Paster B J: Microbial risk indicators of early childhood caries. J Clin Microbiol 2005; 43:5753-5759.

Crielaard W, Zaura E, Schuller A A, Huse S M, Montijn R C, Keijser B J: Exploring the oral microbiota of children at various developmental stages of their dentition in the relation to their oral health. BMC Med Genomics 2011; 4:22.

Dawes C, Dibdin G H: Salivary concentrations of urea released from a chewing gum containing urea and how these affect the urea content of gel-stabilized plaques and their ph after exposure to sucrose. Caries Res 2001; 35:344-353.

Dewhirst F E, Chen T, Izard J, Paster B J, Tanner A C, Yu W H, Lakshmanan A, Wade W G: The human oral microbiome. J Bacteriol 2010; 192:5002-5017.

Dong Y, Chen Y Y, Burne R A: Control of expression of the arginine deiminase operon of streptococcus gordonii by ccpa and flp. J Bacteriol 2004; 186:2511-2514.

Gross E L, Leys E J, Gasparovich S R, Firestone N D, Schwartzbaum J A, Janies D A, Asnani K, Griffen A L: Bacterial 16s sequence analysis of severe caries in young permanent teeth. J Clin Microbiol 2010; 48:4121-4128.

Kleinberg I: Biochemistry of the dental plaque. Advances in oral biology 1970; 4:43-90.

Kleinberg I, Jenkins G N: The ph of dental plaques in the different areas of the mouth before and after meals and their relationship to the ph and rate of flow of resting saliva. Arch Oral Biol 1964; 72:493-516.

Liu Y, Burne R A: Multiple two-component systems modulate alkali generation in streptococcus gordonii in response to environmental stresses. J Bacteriol 2009; 191:7353-7362.

Liu Y, Burne R A: The major autolysin of streptococcus gordonii is subject to complex regulation and modulates stress tolerance, biofilm formation, and extracellular-DNA release. J Bacteriol 2011; 193:2826-2837.

Liu Y, Dong Y, Chen Y Y, Burne R A: Environmental and growth phase regulation of the streptococcus gordonii arginine deiminase genes. Appl Environ Microbiol 2008; 74:5023-5030.

Mager D L, Ximenez-Fyvie L A, Haffajee A D, Socransky S S: Distribution of selected bacterial species on intraoral surfaces. J Clin Periodontol 2003; 30:644-654.

Margolis H C, Duckworth J H, Moreno E C: Composition and buffer capacity of pooled starved plaque fluid from caries-free and caries-susceptible individuals. J Dent Res 1988a; 67:1476-1482.

Margolis H C, Duckworth J H, Moreno E C: Composition and buffer capacity of pooled starved plaque fluid from caries-free and caries-susceptible individuals. J Dent Res 1988b; 67:1476-1482.

Marquis R E: Oxygen metabolism, oxidative stress and acid-base physiology of dental plaque biofilms. Journal of industrial microbiology 1995; 15:198-207.

Marquis R E, Bender G R, Murray D R, Wong A: Arginine deiminase system and bacterial adaptation to acid environments. Appl Environ Microbiol 1987a; 53:198-200.

Marquis R E, Bender G R, Murray D R, Wong A: Arginine deiminase system and bacterial adaptation to acid environments. Appl Environ Microbiol 1987b; 53:198-200.

Nascimento M M, Gordan W, Garvan C W, Browngardt C M, Burne R A: Correlations of oral bacterial arginine and urea catabolism with caries experience. Oral Microbiol Immunol 2009a; 24:89-95.

Nascimento M M, Gordan W, Garvan C W, Browngardt C M, Burne R A: Correlations of oral bacterial arginine and urea catabolism with caries experience. Oral Microbiol Immunol 2009b; 24:89-95.

Nascimento M M, Liu Y, Kalra R, Perez S, Adewumi A, Xu X, Burne R A: Arginine metabolism may confer caries resistance in children. J Dent Res 2012; 91:691.

Paster B J, Boches S K, Galvin J L, Ericson R E, Lau C N, Levanos V A, Sahasrabudhe A, Dewhirst F E: Bacterial diversity in human subgingival plaque. J Bacteriol 2001; 183:3770-3783.

Peterson P: Research for oral health in developing countires.; in: WHO Global Forum for Health Research. Mexico city, Mexico, 2004.

Peterson S, Woodhead J, Crall J: Caries resistance in children with chronic renal failure: Plaque ph, salivary ph, and salivary composition. Pediatr Res 1985; 19:796-799.

Rogers A H: Utilization of nitrogenous compounds by oral bacteria. Aust Dent J 1990; 35:468-471.

Russell R R: How has genomics altered our view of caries microbiology? Caries Res 2008; 42:319-327.

Schulte R, Burne R A, Gordan W, Nascimento M M: Alkali generation capacity of oral bacteria J Dent Res 2009; 88:1183.

Shu M, Morou-Bermudez E, Suarez-Perez E, Rivera-Miranda C, Browngardt C M, Chen Y Y, Magnusson I, Burne R A: The relationship between dental caries status and dental plaque urease activity. Oral Microbiol Immunol 2007a; 22:61-66.

Shu M, Morou-Bermudez E, Suarez-Perez E, Rivera-Miranda C, Browngardt C M, Chen Y Y, Magnusson I, Burne R A: The relationship between dental caries status and dental plaque urease activity. Oral Microbiol Immunol 2007b; 22:61-66.

Sissons C H, Hancock E M, Cutress T W: The source of variation in ureolysis in artificial plaques cultured from human salivary bacteria. Arch Oral Biol 1988a; 33:721-726.

Sissons C H, Hancock E M, Perinpanayagam H E, Cutress T W: The bacteria responsible for ureolysis in artificial dental plaque. Arch Oral Biol 1988b; 33:727-733.

Sissons C H, Wong L, Hancock E M, Cutress T W: The ph response to urea and the effect of liquid flow in 'artificial mouth' microcosm plaques. Arch Oral Biol 1994; 39:497-505.

Stephan R M: Changes in hydrogen-ion concentration on tooth surfaces and in carious lesions. J Am Dent Assoc 1940; 27:718-723.

Van Wuyckhuyse B C, Perinpanayagam H E, Bevacqua D, Raubertas R F, Billings R J, Bowen W H, Tabak L A: Association of free arginine and lysine concentrations in human parotid saliva with caries experience. J Dent Res 1995; 74:686-690.

Vander Wauven C, Pierard A, Kley-Raymann M, Haas D: *Pseudomonas aeruginosa* mutants affected in anaerobic growth on arginine: Evidence for a four-gene cluster encoding the arginine deiminase pathway. J Bacteriol 1984; 160:928-934.

Wijeyeweera R L, Kleinberg I: Arginolytic and ureolytic activities of pure cultures of human oral bacteria and their effects on the ph response of salivary sediment and dental plaque in vitro. Arch Oral Biol 1989a; 34:43-53.

Wijeyeweera R L, Kleinberg I: Arginolytic and ureolytic activities of pure cultures of human oral bacteria and their effects on the ph response of salivary sediment and dental plaque in vitro. Arch Oral Biol 1989b; 34:43-53.

Text Copy of the Sequence Listing

The following is a listing of sequences appearing in the present application:

```
<210> 1
<211> 20
<212> DNA
<213> artificial

<220>
<223> chemically synthesized forward 16S rRNA
      sequence

<400> 1
agagtttgat cctggctcag                                         20

<210> 2
<211> 21
<212> DNA
<213> artificial

<220>
<223> chemically synthesized reverse 16S rRNA
      sequence

<400> 2
tacgggtacc ttgttacgac t                                       21
```

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: chemically synthesized forward 16S rRNA
      sequence

<400> SEQUENCE: 1
agagtttgat cctggctcag                                                     20

<210> SEQ ID NO 2
<211> LENGTH: 21
<212> TYPE: DNA
<213> ORGANISM: Artificial Sequence
<220> FEATURE:
<223> OTHER INFORMATION: chemically synthesized reverse 16S rRNA
      sequence

<400> SEQUENCE: 2
tacgggtacc ttgttacgac t                                                   21
```

The invention claimed is:

1. A method for making a mixture of arginolytic bacterial strains for oral use, the method comprising:
   (a) obtaining a mixture of bacterial strains isolated from oral samples;
   (b) isolating and identifying arginolytic bacterial strains capable of producing ammonia via the arginine deiminase system (ADS);
   (c) conducting one or more separate assays to identify arginolytic bacterial strains capable of expressing ADS activity in at least one of the following assay conditions: in the absence of environmental arginine, in the presence of glucose, in a non-acidic pH, in aerobic conditions, and in the presence of at least one bacterial strain associated with dental caries;
   (d) selecting at least two different isolated arginolytic bacterial strains identified in step (c) to prepare a mixture of arginolytic bacteria; and
   (e) preparing a mixture of the at least two isolated arginolytic bacterial strains, wherein the mixture expresses ADS activity in at least two of the conditions, and wherein the mixture does not include any strains of *Streptococcus mutans*.

2. The method of claim 1, wherein the ability of the bacterial strain to express ADS activity in any of said assay conditions is determined with respect to the ADS activity level of *S. gordonii* DL1 under the same conditions, wherein an ADS activity level about the same or higher than the activity of *S. gordonii* DL1 under the same conditions indicates the strain expresses ADS activity under the conditions.

3. The method of claim 1, wherein the bacterial strain associated with dental caries is *Streptococcus mutans*.

4. The method of claim 1, further comprising including in the mixture one or more compounds capable of increasing the ADS activity of the bacterial strains with respect to the ADS activity of the strains in the absence of the compounds.

5. The method of claim 4, wherein the one or more compounds to increase the ADS activity of the bacterial strains are selected from the group consisting of: galactose, arginine, and an acidic compound.

* * * * *

UNITED STATES PATENT AND TRADEMARK OFFICE
CERTIFICATE OF CORRECTION

| | | |
|---|---|---|
| PATENT NO. | : 9,655,839 B2 | Page 1 of 1 |
| APPLICATION NO. | : 14/767181 | |
| DATED | : May 23, 2017 | |
| INVENTOR(S) | : Marcelle Matos Nascimento Fegerberg and Robert A. Burne | |

It is certified that error appears in the above-identified patent and that said Letters Patent is hereby corrected as shown below:

In the Specification

Column 1 Lines 20-23:
Change:
"This invention was made with Govermnent support under 20 Contract No.: DE10362 awarded by the National Institute of Dental and Craniofacial Research. The Govermnent has certain rights in this invention."

To:
-- This invention was made with government support under DE010362 awarded by The National Institutes of Health. The government has certain rights in the invention. --

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*